(12) United States Patent
Handique

(10) Patent No.: US 10,139,012 B2
(45) Date of Patent: Nov. 27, 2018

(54) INTEGRATED HEATER AND MAGNETIC SEPARATOR

(71) Applicant: HandyLab, Inc., Franklin Lakes, NJ (US)

(72) Inventor: Kalyan Handique, Ypsilanti, MI (US)

(73) Assignee: HandyLab, Inc., Franklin Lakes, NJ (US)

( * ) Notice: Subject to any disclaimer, the term of this patent is extended or adjusted under 35 U.S.C. 154(b) by 0 days.

(21) Appl. No.: 15/482,572

(22) Filed: Apr. 7, 2017

(65) Prior Publication Data

US 2018/0017184 A1   Jan. 18, 2018

Related U.S. Application Data

(63) Continuation of application No. 12/178,586, filed on Jul. 23, 2008, now Pat. No. 9,618,139, which is a
(Continued)

(51) Int. Cl.
*G01N 35/00* (2006.01)
*F16K 99/00* (2006.01)
(Continued)

(52) U.S. Cl.
CPC ............ *F16K 99/0001* (2013.01); *B01L 7/52* (2013.01); *B01L 9/527* (2013.01); *F16K 99/003* (2013.01); *F16K 99/0032* (2013.01); *F16K 99/0044* (2013.01); *F16K 99/0061* (2013.01); *B01L 3/5027* (2013.01); *B01L 2200/147* (2013.01); *B01L 2200/148* (2013.01); *B01L 2200/16* (2013.01); *B01L 2300/021* (2013.01); *B01L 2300/1822* (2013.01); *B01L 2300/1827* (2013.01); *B01L 2300/1861* (2013.01);
(Continued)

(58) Field of Classification Search
CPC ........ G01N 35/0098; B03C 1/06; B03C 1/12; B03C 1/288
See application file for complete search history.

(56) References Cited

U.S. PATENT DOCUMENTS

D189,404 S   12/1960  Nicolle
3,050,239 A   8/1962  Williams
(Continued)

FOREIGN PATENT DOCUMENTS

CA    2294819      1/1999
CN    1968754 A    5/2007
(Continued)

OTHER PUBLICATIONS

International Search Report and Written Opinion dated Jan. 5, 2009 for PCT/US2007/024022, filed Nov. 14, 2007.
(Continued)

*Primary Examiner* — Jonathan M Hurst
(74) *Attorney, Agent, or Firm* — Knobbe Martens Olson & Bear LLP

(57) ABSTRACT

An apparatus for providing thermal and magnetic energy to a receptacle containing a reaction mixture and a magnetic retention member. The apparatus can also control heating of a reaction mixture, and bring about a separation of magnetic particles from the reaction mixture. The reaction mixture typically comprises polynucleotides from a biological sample that are being brought into a PCR-ready form.

18 Claims, 7 Drawing Sheets

Related U.S. Application Data continuation-in-part of application No. 12/218,498, filed on Jul. 14, 2008, now Pat. No. 9,186,677, and a continuation-in-part of application No. 12/173,023, filed on Jul. 14, 2008, now Pat. No. 8,133,671.

(60) Provisional application No. 60/959,437, filed on Jul. 13, 2007.

(51) Int. Cl.
  *B01L 9/00* (2006.01)
  *B01L 7/00* (2006.01)
  *B03C 1/12* (2006.01)
  *B03C 1/28* (2006.01)
  *B03C 1/06* (2006.01)
  *B01L 3/00* (2006.01)

(52) U.S. Cl.
  CPC  *B03C 1/06* (2013.01); *B03C 1/12* (2013.01); *B03C 1/288* (2013.01); *F16K 2099/0084* (2013.01); *G01N 35/0098* (2013.01); *G01N 2035/00881* (2013.01)

(56) References Cited

U.S. PATENT DOCUMENTS

| | | |
|---|---|---|
| 3,905,772 A | 9/1975 | Hartnett et al. |
| 3,985,649 A | 10/1976 | Eddelman |
| 4,018,089 A | 4/1977 | Dzula et al. |
| 4,018,652 A | 4/1977 | Lanham et al. |
| 4,038,192 A | 7/1977 | Serur |
| 4,055,395 A | 10/1977 | Honkawa et al. |
| D249,706 S | 9/1978 | Adamski |
| 4,139,005 A | 2/1979 | Dickey |
| D252,157 S | 6/1979 | Kronish et al. |
| D252,341 S | 7/1979 | Thomas |
| D254,687 S | 4/1980 | Fadler et al. |
| 4,212,744 A | 7/1980 | Oota |
| D261,033 S | 9/1981 | Armbruster |
| D261,173 S | 10/1981 | Armbruster |
| 4,301,412 A | 11/1981 | Hill et al. |
| 4,439,526 A | 3/1984 | Columbus |
| 4,457,329 A | 7/1984 | Werley et al. |
| 4,466,740 A | 8/1984 | Kano et al. |
| 4,472,357 A | 9/1984 | Levy et al. |
| 4,504,582 A | 3/1985 | Swann |
| 4,522,786 A | 6/1985 | Ebersole |
| D279,817 S | 7/1985 | Chen et al. |
| D282,208 S | 1/1986 | Lowry |
| 4,599,315 A | 7/1986 | Terasaki et al. |
| 4,612,873 A | 9/1986 | Eberle |
| 4,612,959 A | 9/1986 | Costello |
| D288,478 S | 2/1987 | Carlson et al. |
| 4,647,432 A | 3/1987 | Wakatake |
| 4,654,127 A | 3/1987 | Baker et al. |
| 4,673,657 A | 6/1987 | Christian |
| 4,678,752 A | 7/1987 | Thorne et al. |
| 4,683,195 A | 7/1987 | Mullis et al. |
| 4,683,202 A | 7/1987 | Mullis |
| D292,735 S | 11/1987 | Lovborg |
| 4,720,374 A | 1/1988 | Ramachandran |
| 4,724,207 A | 2/1988 | Hou et al. |
| 4,798,693 A | 1/1989 | Mase et al. |
| 4,800,022 A | 1/1989 | Leonard |
| 4,827,944 A | 5/1989 | Nugent |
| 4,841,786 A | 6/1989 | Schulz |
| D302,294 S | 7/1989 | Hillman |
| 4,855,110 A | 8/1989 | Marker et al. |
| 4,871,779 A | 10/1989 | Killat et al. |
| 4,895,650 A | 1/1990 | Wang |
| 4,919,829 A | 4/1990 | Gates et al. |
| 4,921,809 A | 5/1990 | Schiff et al. |
| 4,935,342 A | 6/1990 | Seligson et al. |
| 4,946,562 A | 8/1990 | Guruswamy |
| 4,949,742 A | 8/1990 | Rando et al. |
| D310,413 S | 9/1990 | Bigler et al. |
| 4,963,498 A | 10/1990 | Hillman |
| 4,967,950 A | 11/1990 | Legg et al. |
| D312,692 S | 12/1990 | Bradley |
| 4,978,502 A | 12/1990 | Dole et al. |
| 4,978,622 A | 12/1990 | Mishell et al. |
| 4,989,626 A | 2/1991 | Takagi et al. |
| 5,001,417 A | 3/1991 | Pumphrey et al. |
| 5,004,583 A | 4/1991 | Guruswamy et al. |
| 5,048,554 A | 9/1991 | Kremer |
| 5,053,199 A | 10/1991 | Keiser et al. |
| 5,060,823 A | 10/1991 | Perlman |
| 5,061,336 A | 10/1991 | Soane |
| 5,064,618 A | 11/1991 | Baker et al. |
| 5,071,531 A | 12/1991 | Soane |
| 5,091,328 A | 2/1992 | Miller |
| D324,426 S | 3/1992 | Fan et al. |
| 5,096,669 A | 3/1992 | Lauks et al. |
| D325,638 S | 4/1992 | Sloat et al. |
| 5,126,002 A | 6/1992 | Iwata et al. |
| 5,126,022 A | 6/1992 | Soane et al. |
| D328,135 S | 7/1992 | Fan et al. |
| D328,794 S | 8/1992 | Frenkel et al. |
| 5,135,627 A | 8/1992 | Soane |
| 5,135,872 A | 8/1992 | Pouletty et al. |
| 5,147,606 A | 9/1992 | Charlton et al. |
| 5,169,512 A | 12/1992 | Wiedenmann et al. |
| D333,522 S | 2/1993 | Gianino |
| 5,186,339 A | 2/1993 | Heissler |
| 5,192,507 A | 3/1993 | Taylor et al. |
| 5,208,163 A | 5/1993 | Charlton et al. |
| 5,217,694 A | 6/1993 | Gibler et al. |
| 5,223,226 A | 6/1993 | Wittmer et al. |
| 5,229,297 A | 7/1993 | Schnipelsky et al. |
| D338,275 S | 8/1993 | Fischer et al. |
| 5,250,263 A | 10/1993 | Manz |
| 5,252,743 A | 10/1993 | Barrett et al. |
| 5,256,376 A | 10/1993 | Callan et al. |
| 5,275,787 A | 1/1994 | Yuguchi et al. |
| 5,282,950 A | 2/1994 | Dietze et al. |
| 5,296,375 A | 3/1994 | Kricka et al. |
| 5,304,477 A | 4/1994 | Nagoh et al. |
| 5,304,487 A | 4/1994 | Wilding et al. |
| D347,478 S | 5/1994 | Pinkney |
| 5,311,896 A | 5/1994 | Kaartinen et al. |
| 5,311,996 A | 5/1994 | Duffy et al. |
| 5,316,727 A | 5/1994 | Suzuki et al. |
| 5,327,038 A | 7/1994 | Culp |
| 5,339,486 A | 8/1994 | Persic, Jr. |
| D351,475 S | 10/1994 | Gerber |
| D351,913 S | 10/1994 | Hieb et al. |
| 5,364,591 A | 11/1994 | Green et al. |
| 5,372,946 A | 12/1994 | Cusak et al. |
| 5,374,395 A | 12/1994 | Robinson |
| 5,389,339 A | 2/1995 | Petschek et al. |
| D356,232 S | 3/1995 | Armstrong et al. |
| 5,397,709 A | 3/1995 | Berndt |
| 5,401,465 A | 3/1995 | Smethers et al. |
| 5,411,708 A | 5/1995 | Moscetta et al. |
| 5,414,245 A | 5/1995 | Hackleman |
| 5,415,839 A | 5/1995 | Zaun et al. |
| 5,416,000 A | 5/1995 | Allen et al. |
| 5,422,271 A | 6/1995 | Chen et al. |
| 5,422,284 A | 6/1995 | Lau |
| 5,427,946 A | 6/1995 | Kricka et al. |
| 5,443,791 A | 8/1995 | Cathcart et al. |
| 5,474,796 A | 12/1995 | Brennan |
| D366,116 S | 1/1996 | Biskupski |
| 5,486,335 A | 1/1996 | Wilding et al. |
| 5,494,639 A | 2/1996 | Grzegorzewski |
| 5,498,392 A | 3/1996 | Wilding et al. |
| 5,503,803 A | 4/1996 | Brown |
| 5,516,410 A | 5/1996 | Schneider et al. |
| 5,519,635 A | 5/1996 | Miyake et al. |
| 5,529,677 A | 6/1996 | Schneider et al. |
| 5,559,432 A | 9/1996 | Logue |
| 5,565,171 A | 10/1996 | Dovichi et al. |
| 5,569,364 A | 10/1996 | Hooper et al. |

(56) References Cited

U.S. PATENT DOCUMENTS

| | | |
|---|---|---|
| 5,578,270 A | 11/1996 | Reichler et al. |
| 5,578,818 A | 11/1996 | Kain et al. |
| 5,579,928 A | 12/1996 | Anukwuem |
| 5,580,523 A | 12/1996 | Bard |
| 5,582,884 A | 12/1996 | Ball et al. |
| 5,582,988 A | 12/1996 | Backus et al. |
| 5,585,069 A | 12/1996 | Zanucchi et al. |
| 5,585,089 A | 12/1996 | Queen et al. |
| 5,585,242 A | 12/1996 | Bouma et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,595,708 A | 1/1997 | Berndt |
| 5,599,432 A | 2/1997 | Manz et al. |
| 5,599,503 A | 2/1997 | Manz et al. |
| 5,599,667 A | 2/1997 | Arnold, Jr. et al. |
| 5,601,727 A | 2/1997 | Bormann et al. |
| 5,603,351 A | 2/1997 | Cherukuri et al. |
| 5,605,662 A | 2/1997 | Heller et al. |
| 5,609,910 A | 3/1997 | Hackleman |
| D378,782 S | 4/1997 | LaBarbera et al. |
| 5,628,890 A | 5/1997 | Carter et al. |
| 5,630,920 A | 5/1997 | Friese et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,639,428 A | 6/1997 | Cottingham |
| 5,643,738 A | 7/1997 | Zanzucchi et al. |
| 5,645,801 A | 7/1997 | Bouma et al. |
| 5,646,039 A | 7/1997 | Northrup et al. |
| 5,646,049 A | 7/1997 | Tayi |
| 5,647,994 A | 7/1997 | Tuunanen et al. |
| 5,651,839 A | 7/1997 | Rauf |
| 5,652,141 A | 7/1997 | Henco et al. |
| 5,652,149 A | 7/1997 | Mileaf et al. |
| D382,346 S | 8/1997 | Buhler et al. |
| D382,647 S | 8/1997 | Staples et al. |
| 5,667,976 A | 9/1997 | Van Ness et al. |
| 5,671,303 A | 9/1997 | Shieh et al. |
| 5,674,394 A | 10/1997 | Whitmore |
| 5,674,742 A | 10/1997 | Northrup et al. |
| 5,681,484 A | 10/1997 | Zanzucchi et al. |
| 5,681,529 A | 10/1997 | Taguchi et al. |
| 5,683,657 A | 11/1997 | Mian |
| 5,699,157 A | 12/1997 | Parce et al. |
| 5,700,637 A | 12/1997 | Southern |
| 5,705,813 A | 1/1998 | Apffel et al. |
| 5,721,136 A | 2/1998 | Finney et al. |
| 5,725,831 A | 3/1998 | Reichler et al. |
| 5,726,026 A | 3/1998 | Wilding et al. |
| 5,726,404 A | 3/1998 | Brody |
| 5,726,944 A | 3/1998 | Pelley et al. |
| 5,731,212 A | 3/1998 | Gavin et al. |
| 5,744,366 A | 4/1998 | Kricka et al. |
| 5,746,978 A | 5/1998 | Bienhaus et al. |
| 5,747,666 A | 5/1998 | Willis |
| 5,750,015 A | 5/1998 | Soane et al. |
| 5,755,942 A | 5/1998 | Zanzucchi et al. |
| 5,762,874 A | 6/1998 | Seaton et al. |
| 5,763,262 A | 6/1998 | Wong et al. |
| 5,770,029 A | 6/1998 | Nelson et al. |
| 5,770,388 A | 6/1998 | Vorpahl |
| 5,772,966 A | 6/1998 | Maracas et al. |
| 5,779,868 A | 7/1998 | Parce et al. |
| 5,783,148 A | 7/1998 | Cottingham et al. |
| 5,787,032 A | 7/1998 | Heller et al. |
| 5,788,814 A | 8/1998 | Sun et al. |
| 5,800,600 A | 9/1998 | Lima-Marques et al. |
| 5,800,690 A | 9/1998 | Chow et al. |
| 5,804,436 A | 9/1998 | Okun et al. |
| D399,959 S | 10/1998 | Prokop et al. |
| 5,827,481 A | 10/1998 | Bente et al. |
| 5,842,106 A | 11/1998 | Thaler et al. |
| 5,842,787 A | 12/1998 | Kopf-Sill et al. |
| 5,846,396 A | 12/1998 | Zanzucchi et al. |
| 5,846,493 A | 12/1998 | Bankier et al. |
| 5,849,208 A | 12/1998 | Hayes et al. |
| 5,849,486 A | 12/1998 | Heller et al. |
| 5,849,489 A | 12/1998 | Heller |
| 5,849,598 A | 12/1998 | Wilson et al. |
| 5,852,495 A | 12/1998 | Parce |
| 5,856,174 A | 1/1999 | Lipshutz et al. |
| 5,858,187 A | 1/1999 | Ramsey et al. |
| 5,858,188 A | 1/1999 | Soane et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |
| 5,869,244 A | 2/1999 | Martin et al. |
| 5,872,010 A | 2/1999 | Karger et al. |
| 5,872,623 A | 2/1999 | Stabile et al. |
| 5,874,046 A | 2/1999 | Megerle |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,432 A | 3/1999 | Hooper et al. |
| 5,885,470 A | 3/1999 | Parce et al. |
| 5,895,762 A | 4/1999 | Greenfield et al. |
| 5,900,130 A | 5/1999 | Benvegnu et al. |
| 5,912,124 A | 6/1999 | Kumar |
| 5,912,134 A | 6/1999 | Shartle |
| 5,914,229 A | 6/1999 | Loewy |
| 5,916,522 A | 6/1999 | Boyd et al. |
| 5,916,776 A | 6/1999 | Kumar |
| 5,919,646 A | 7/1999 | Okun et al. |
| 5,919,711 A | 7/1999 | Boyd et al. |
| 5,922,591 A | 7/1999 | Anderson et al. |
| 5,927,547 A | 7/1999 | Papen et al. |
| 5,928,880 A | 7/1999 | Wilding et al. |
| 5,929,208 A | 7/1999 | Heller et al. |
| D413,391 S | 8/1999 | Lapeus et al. |
| 5,932,799 A | 8/1999 | Moles |
| 5,935,401 A | 8/1999 | Amigo |
| 5,939,291 A | 8/1999 | Loewy et al. |
| 5,939,312 A | 8/1999 | Baier et al. |
| 5,942,443 A | 8/1999 | Parce et al. |
| D413,677 S | 9/1999 | Dumitrescu et al. |
| D414,271 S | 9/1999 | Mendoza |
| 5,948,227 A | 9/1999 | Dubrow |
| 5,948,363 A | 9/1999 | Gaillard |
| 5,948,673 A | 9/1999 | Cottingham |
| 5,955,028 A | 9/1999 | Chow |
| 5,955,029 A | 9/1999 | Wilding et al. |
| 5,957,579 A | 9/1999 | Kopf-Sill et al. |
| 5,958,203 A | 9/1999 | Parce et al. |
| 5,958,694 A | 9/1999 | Nikiforov |
| 5,959,221 A | 9/1999 | Boyd et al. |
| 5,959,291 A | 9/1999 | Jensen |
| 5,964,995 A | 10/1999 | Nikiforov et al. |
| 5,964,997 A | 10/1999 | McBride |
| 5,965,001 A | 10/1999 | Chow et al. |
| 5,965,410 A | 10/1999 | Chow et al. |
| 5,965,886 A | 10/1999 | Sauer et al. |
| 5,968,745 A | 10/1999 | Thorp et al. |
| 5,972,187 A | 10/1999 | Parce et al. |
| 5,973,138 A | 10/1999 | Collis |
| D417,009 S | 11/1999 | Boyd |
| 5,976,336 A | 11/1999 | Dubrow et al. |
| 5,980,704 A | 11/1999 | Cherukuri et al. |
| 5,980,719 A | 11/1999 | Cherukuri et al. |
| 5,981,735 A | 11/1999 | Thatcher et al. |
| 5,989,402 A | 11/1999 | Chow et al. |
| 5,992,820 A | 11/1999 | Fare et al. |
| 5,993,611 A | 11/1999 | Moroney, III et al. |
| 5,993,750 A | 11/1999 | Ghosh et al. |
| 5,997,708 A | 12/1999 | Craig |
| 6,001,229 A | 12/1999 | Ramsey |
| 6,001,231 A | 12/1999 | Kopf-Sill |
| 6,001,307 A | 12/1999 | Naka et al. |

(56) References Cited

U.S. PATENT DOCUMENTS

| | | |
|---|---|---|
| 6,004,515 A | 12/1999 | Parce et al. |
| 6,007,690 A | 12/1999 | Nelson et al. |
| 6,010,607 A | 1/2000 | Ramsey |
| 6,010,608 A | 1/2000 | Ramsey |
| 6,010,627 A | 1/2000 | Hood, III |
| 6,012,902 A | 1/2000 | Parce |
| D420,747 S | 2/2000 | Dumitrescu et al. |
| D421,130 S | 2/2000 | Cohen et al. |
| 6,024,920 A | 2/2000 | Cunanan |
| D421,653 S | 3/2000 | Purcell |
| 6,033,546 A | 3/2000 | Ramsey |
| 6,033,880 A | 3/2000 | Haff et al. |
| 6,043,080 A | 3/2000 | Lipshutz et al. |
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,062,261 A | 5/2000 | Jacobson et al. |
| 6,063,341 A | 5/2000 | Fassbind et al. |
| 6,063,589 A | 5/2000 | Kellogg et al. |
| 6,068,752 A | 5/2000 | Dubrow et al. |
| 6,071,478 A | 6/2000 | Chow |
| 6,074,725 A | 6/2000 | Kennedy |
| 6,074,827 A | 6/2000 | Nelson et al. |
| D428,497 S | 7/2000 | Lapeus et al. |
| 6,086,740 A | 7/2000 | Kennedy |
| 6,096,509 A | 8/2000 | Okun et al. |
| 6,100,541 A | 8/2000 | Nagle et al. |
| 6,102,897 A | 8/2000 | Lang |
| 6,103,537 A | 8/2000 | Ullman et al. |
| 6,106,685 A | 8/2000 | McBride et al. |
| 6,110,343 A | 8/2000 | Ramsey et al. |
| 6,117,398 A | 9/2000 | Bienhaus et al. |
| 6,123,205 A | 9/2000 | Dumitrescu et al. |
| 6,123,798 A | 9/2000 | Gandhi et al. |
| 6,130,098 A | 10/2000 | Handique et al. |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,149,787 A | 11/2000 | Chow et al. |
| 6,149,872 A | 11/2000 | MacK et al. |
| 6,156,199 A | 12/2000 | Zuk, Jr. |
| 6,158,269 A | 12/2000 | Dorenkott et al. |
| 6,167,910 B1 | 1/2001 | Chow |
| 6,168,948 B1 | 1/2001 | Anderson et al. |
| 6,171,850 B1 | 1/2001 | Nagle et al. |
| 6,174,675 B1 | 1/2001 | Chow et al. |
| 6,180,950 B1 | 1/2001 | Olsen |
| D438,311 S | 2/2001 | Yamanishi et al. |
| 6,190,619 B1 | 2/2001 | Kilcoin et al. |
| 6,194,563 B1 | 2/2001 | Cruickshank |
| D438,632 S | 3/2001 | Miller |
| D438,633 S | 3/2001 | Miller |
| D439,673 S | 3/2001 | Brophy et al. |
| 6,197,595 B1 | 3/2001 | Anderson et al. |
| 6,211,989 B1 | 4/2001 | Wulf et al. |
| 6,213,151 B1 | 4/2001 | Jacobson et al. |
| 6,221,600 B1 | 4/2001 | MacLeod et al. |
| 6,228,635 B1 | 5/2001 | Armstrong et al. |
| 6,232,072 B1 | 5/2001 | Fisher |
| 6,235,175 B1 | 5/2001 | Dubrow et al. |
| 6,235,313 B1 | 5/2001 | Mathiowitz et al. |
| 6,235,471 B1 | 5/2001 | Knapp et al. |
| 6,236,456 B1 | 5/2001 | Giebeler et al. |
| 6,236,581 B1 | 5/2001 | Foss et al. |
| 6,238,626 B1 | 5/2001 | Higuchi et al. |
| 6,251,343 B1 | 6/2001 | Dubrow et al. |
| 6,254,826 B1 | 7/2001 | Acosta et al. |
| 6,259,635 B1 | 7/2001 | Khouri et al. |
| 6,261,431 B1 | 7/2001 | Mathies et al. |
| 6,267,858 B1 | 7/2001 | Parce et al. |
| D446,306 S | 8/2001 | Ochi et al. |
| 6,271,021 B1 | 8/2001 | Burns et al. |
| 6,274,089 B1 | 8/2001 | Chow et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,284,470 B1 | 9/2001 | Bitner et al. |
| 6,287,254 B1 | 9/2001 | Dodds |
| 6,287,774 B1 | 9/2001 | Nikiforov |
| 6,291,248 B1 | 9/2001 | Haj-Ahmad |
| 6,294,063 B1 | 9/2001 | Becker et al. |
| 6,302,134 B1 | 10/2001 | Kellogg et al. |
| 6,302,304 B1 | 10/2001 | Spencer |
| 6,303,343 B1 | 10/2001 | Kopf-sill |
| 6,306,273 B1 | 10/2001 | Wainright et al. |
| 6,306,590 B1 | 10/2001 | Mehta et al. |
| 6,310,199 B1 | 10/2001 | Smith et al. |
| 6,316,774 B1 | 11/2001 | Giebeler et al. |
| 6,319,469 B1 | 11/2001 | Mian et al. |
| 6,322,683 B1 | 11/2001 | Wolk et al. |
| 6,326,083 B1 | 12/2001 | Yang et al. |
| 6,326,147 B1 | 12/2001 | Oldham et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-sill et al. |
| 6,366,924 B1 | 4/2002 | Parce |
| 6,368,561 B1 | 4/2002 | Rutishauser et al. |
| 6,368,871 B1 | 4/2002 | Christel et al. |
| 6,370,206 B1 | 4/2002 | Schenk |
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,382,254 B1 | 5/2002 | Yang et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Maher et al. |
| 6,401,552 B1 | 6/2002 | Elkins |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-sill |
| 6,425,972 B1 | 7/2002 | McReynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,064 B1 | 9/2002 | Vo-Dinh et al. |
| 6,453,928 B1 | 9/2002 | Kaplan et al. |
| 6,458,259 B1 | 10/2002 | Parce et al. |
| 6,461,570 B2 | 10/2002 | Ishihara et al. |
| 6,465,257 B1 | 10/2002 | Parce et al. |
| 6,468,761 B2 | 10/2002 | Yang et al. |
| 6,472,141 B2 | 10/2002 | Nikiforov |
| D466,219 S | 11/2002 | Wynschenk et al. |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,193 B1 | 1/2003 | Tajima |

(56) References Cited

U.S. PATENT DOCUMENTS

| | | | |
|---|---|---|---|
| 6,511,853 | B1 | 1/2003 | Kopf-sill et al. |
| D470,595 | S | 2/2003 | Crisanti et al. |
| 6,515,753 | B2 | 2/2003 | Maher |
| 6,517,783 | B2 | 2/2003 | Horner et al. |
| 6,520,197 | B2 | 2/2003 | Deshmukh et al. |
| 6,521,188 | B1 | 2/2003 | Webster |
| 6,524,456 | B1 | 2/2003 | Ramsey et al. |
| 6,524,790 | B1 | 2/2003 | Kopf-sill et al. |
| D472,324 | S | 3/2003 | Rumore et al. |
| 6,534,295 | B2 | 3/2003 | Tai et al. |
| 6,537,771 | B1 | 3/2003 | Farinas et al. |
| 6,540,896 | B1 | 4/2003 | Manz et al. |
| 6,544,734 | B1 | 4/2003 | Briscoe et al. |
| 6,547,942 | B1 | 4/2003 | Parce et al. |
| 6,555,389 | B1 | 4/2003 | Ullman et al. |
| 6,556,923 | B2 | 4/2003 | Gallagher et al. |
| D474,279 | S | 5/2003 | Mayer et al. |
| D474,280 | S | 5/2003 | Niedbala et al. |
| 6,558,916 | B2 | 5/2003 | Veerapandian et al. |
| 6,558,945 | B1 | 5/2003 | Kao |
| 6,569,607 | B2 | 5/2003 | McReynolds |
| 6,572,830 | B1 | 6/2003 | Burdon et al. |
| 6,575,188 | B2 | 6/2003 | Parunak |
| 6,576,459 | B2 | 6/2003 | Miles et al. |
| 6,579,453 | B1 | 6/2003 | Bächler et al. |
| 6,589,729 | B2 | 7/2003 | Chan et al. |
| 6,592,821 | B1 | 7/2003 | Wada et al. |
| 6,597,450 | B1 | 7/2003 | Andrews et al. |
| 6,602,474 | B1 | 8/2003 | Tajima |
| 6,613,211 | B1 | 9/2003 | Mccormick et al. |
| 6,613,512 | B1 | 9/2003 | Kopf-sill et al. |
| 6,613,580 | B1 | 9/2003 | Chow et al. |
| 6,613,581 | B1 | 9/2003 | Wada et al. |
| 6,614,030 | B2 | 9/2003 | Maher et al. |
| 6,620,625 | B2 | 9/2003 | Wolk et al. |
| 6,623,860 | B2 | 9/2003 | Hu et al. |
| 6,627,406 | B1 | 9/2003 | Singh et al. |
| D480,814 | S | 10/2003 | Lafferty et al. |
| 6,632,655 | B1 | 10/2003 | Mehta et al. |
| 6,633,785 | B1 | 10/2003 | Kasahara et al. |
| D482,796 | S | 11/2003 | Oyama et al. |
| 6,640,981 | B2 | 11/2003 | Lafond et al. |
| 6,649,358 | B1 | 11/2003 | Parce et al. |
| 6,664,104 | B2 | 12/2003 | Pourahmadi et al. |
| 6,669,831 | B2 | 12/2003 | Chow et al. |
| 6,670,153 | B2 | 12/2003 | Stern |
| D484,989 | S | 1/2004 | Gebrian |
| 6,672,458 | B2 | 1/2004 | Hansen et al. |
| 6,681,616 | B2 | 1/2004 | Spaid et al. |
| 6,681,788 | B2 | 1/2004 | Parce et al. |
| 6,685,813 | B2 | 2/2004 | Williams et al. |
| 6,692,700 | B2 | 2/2004 | Handique |
| 6,695,009 | B2 | 2/2004 | Chien et al. |
| 6,699,713 | B2 | 3/2004 | Benett et al. |
| 6,706,519 | B1 | 3/2004 | Kellogg et al. |
| 6,720,148 | B1 | 4/2004 | Nikiforov |
| 6,730,206 | B2 | 5/2004 | Ricco et al. |
| 6,733,645 | B1 | 5/2004 | Chow |
| 6,734,401 | B2 | 5/2004 | Bedingham et al. |
| 6,737,026 | B1 | 5/2004 | Bergh et al. |
| 6,740,518 | B1 | 5/2004 | Duong et al. |
| D491,272 | S | 6/2004 | Alden et al. |
| D491,273 | S | 6/2004 | Biegler et al. |
| D491,276 | S | 6/2004 | Langille |
| 6,750,661 | B2 | 6/2004 | Brooks et al. |
| 6,752,966 | B1 | 6/2004 | Chazan |
| 6,756,019 | B1 | 6/2004 | Dubrow et al. |
| 6,764,859 | B1 | 7/2004 | Kreuwel et al. |
| 6,766,817 | B2 | 7/2004 | Dias da Silva |
| 6,773,567 | B1 | 8/2004 | Wolk |
| 6,777,184 | B2 | 8/2004 | Nikiforov et al. |
| 6,783,962 | B1 | 8/2004 | Olander et al. |
| D495,805 | S | 9/2004 | Lea et al. |
| 6,787,015 | B2 | 9/2004 | Lackritz et al. |
| 6,787,016 | B2 | 9/2004 | Tan et al. |
| 6,787,111 | B2 | 9/2004 | Roach et al. |
| 6,790,328 | B2 | 9/2004 | Jacobson et al. |
| 6,790,330 | B2 | 9/2004 | Gascoyne et al. |
| 6,811,668 | B1 | 11/2004 | Berndt et al. |
| 6,818,113 | B2 | 11/2004 | Williams et al. |
| 6,819,027 | B2 | 11/2004 | Saraf |
| 6,824,663 | B1 | 11/2004 | Boone |
| D499,813 | S | 12/2004 | Wu |
| D500,142 | S | 12/2004 | Crisanti et al. |
| D500,363 | S | 12/2004 | Fanning et al. |
| 6,827,831 | B1 | 12/2004 | Chow et al. |
| 6,827,906 | B1 | 12/2004 | Bjornson et al. |
| 6,838,156 | B1 | 1/2005 | Neyer et al. |
| 6,838,680 | B2 | 1/2005 | Maher et al. |
| 6,852,287 | B2 | 2/2005 | Ganesan |
| 6,858,185 | B1 | 2/2005 | Kopf-sill et al. |
| 6,859,698 | B2 | 2/2005 | Schmeisser |
| 6,861,035 | B2 | 3/2005 | Pham et al. |
| 6,878,540 | B2 | 4/2005 | Pourahmadi et al. |
| 6,878,755 | B2 | 4/2005 | Singh et al. |
| 6,884,628 | B2 | 4/2005 | Hubbell et al. |
| 6,887,693 | B2 | 5/2005 | McMillan et al. |
| 6,893,879 | B2 | 5/2005 | Petersen et al. |
| 6,900,889 | B2 | 5/2005 | Bjornson et al. |
| 6,905,583 | B2 | 6/2005 | Wainright et al. |
| 6,905,612 | B2 | 6/2005 | Dorian et al. |
| 6,906,797 | B1 | 6/2005 | Kao et al. |
| 6,908,594 | B1 | 6/2005 | Schaevitz et al. |
| 6,911,183 | B1 | 6/2005 | Handique et al. |
| 6,914,137 | B2 | 7/2005 | Baker |
| 6,915,679 | B2 | 7/2005 | Chien et al. |
| 6,918,404 | B2 | 7/2005 | Dias da Silva |
| D508,999 | S | 8/2005 | Fanning et al. |
| 6,939,451 | B2 | 9/2005 | Zhao et al. |
| 6,942,771 | B1 | 9/2005 | Kayyem |
| 6,958,392 | B2 | 10/2005 | Fomovskaia et al. |
| D512,155 | S | 11/2005 | Matsumoto |
| 6,964,747 | B2 | 11/2005 | Banerjee et al. |
| 6,977,163 | B1 | 12/2005 | Mehta |
| 6,984,516 | B2 | 1/2006 | Briscoe et al. |
| D515,707 | S | 2/2006 | Sinohara et al. |
| D516,221 | S | 2/2006 | Wohlstadter et al. |
| 7,001,853 | B1 | 2/2006 | Brown et al. |
| 7,004,184 | B2 | 2/2006 | Handique et al. |
| D517,554 | S | 3/2006 | Yanagisawa et al. |
| 7,010,391 | B2 | 3/2006 | Handique et al. |
| 7,023,007 | B2 | 4/2006 | Gallagher |
| 7,024,281 | B1 | 4/2006 | Unno |
| 7,036,667 | B2 | 5/2006 | Greenstein et al. |
| 7,037,416 | B2 | 5/2006 | Parce et al. |
| 7,038,472 | B1 | 5/2006 | Chien |
| 7,039,527 | B2 | 5/2006 | Tripathi et al. |
| 7,040,144 | B2 | 5/2006 | Spaid et al. |
| 7,041,258 | B2 | 5/2006 | Desmond et al. |
| 7,049,558 | B2 | 5/2006 | Baer et al. |
| D523,153 | S | 6/2006 | Akashi et al. |
| 7,055,695 | B2 | 6/2006 | Greenstein et al. |
| 7,060,171 | B1 | 6/2006 | Nikiforov et al. |
| 7,066,586 | B2 | 6/2006 | Dias da Silva |
| 7,069,952 | B1 | 7/2006 | McReynolds et al. |
| 7,072,036 | B2 | 7/2006 | Jones et al. |
| 7,099,778 | B2 | 8/2006 | Chien |
| D528,215 | S | 9/2006 | Malmsater |
| 7,101,467 | B2 | 9/2006 | Spaid |
| 7,105,304 | B1 | 9/2006 | Nikiforov et al. |
| D531,321 | S | 10/2006 | Godfrey et al. |
| 7,118,910 | B2 | 10/2006 | Unger et al. |
| 7,138,032 | B2 | 11/2006 | Gandhi et al. |
| D534,280 | S | 12/2006 | Gomm et al. |
| 7,148,043 | B2 | 12/2006 | Kordunsky et al. |
| 7,150,814 | B1 | 12/2006 | Parce et al. |
| 7,150,999 | B1 | 12/2006 | Shuck |
| D535,403 | S | 1/2007 | Isozaki et al. |
| 7,160,423 | B2 | 1/2007 | Chien et al. |
| 7,161,356 | B1 | 1/2007 | Chien |
| 7,169,277 | B2 | 1/2007 | Ausserer et al. |
| 7,169,618 | B2 | 1/2007 | Skold |
| D537,951 | S | 3/2007 | Okamoto et al. |
| D538,436 | S | 3/2007 | Patadia et al. |

(56) References Cited

U.S. PATENT DOCUMENTS

| | | |
|---|---|---|
| 7,192,557 B2 | 3/2007 | Wu et al. |
| 7,195,986 B1 | 3/2007 | Bousse et al. |
| 7,205,154 B2 | 4/2007 | Corson |
| 7,208,125 B1 | 4/2007 | Dong |
| 7,235,406 B1 | 6/2007 | Woudenberg et al. |
| 7,247,274 B1 | 7/2007 | Chow |
| D548,841 S | 8/2007 | Brownell et al. |
| D549,827 S | 8/2007 | Maeno et al. |
| 7,252,928 B1 | 8/2007 | Hafeman et al. |
| 7,270,786 B2 | 9/2007 | Parunak et al. |
| D554,069 S | 10/2007 | Bolotin et al. |
| D554,070 S | 10/2007 | Bolotin et al. |
| 7,276,208 B2 | 10/2007 | Sevigny et al. |
| 7,276,330 B2 | 10/2007 | Chow et al. |
| 7,288,228 B2 | 10/2007 | Lefebvre |
| D556,914 S | 12/2007 | Okamoto et al. |
| 7,303,727 B1 | 12/2007 | Dubrow et al. |
| D559,995 S | 1/2008 | Handique et al. |
| 7,323,140 B2 | 1/2008 | Handique et al. |
| 7,332,130 B2 | 2/2008 | Handique |
| 7,338,760 B2 | 3/2008 | Gong et al. |
| D566,291 S | 4/2008 | Parunak et al. |
| 7,351,377 B2 | 4/2008 | Chazan et al. |
| D569,526 S | 5/2008 | Duffy et al. |
| 7,374,949 B2 | 5/2008 | Kuriger |
| 7,390,460 B2 | 6/2008 | Osawa et al. |
| 7,419,784 B2 | 9/2008 | Dubrow et al. |
| 7,422,669 B2 | 9/2008 | Jacobson et al. |
| 7,440,684 B2 | 10/2008 | Spaid et al. |
| 7,476,313 B2 | 1/2009 | Siddiqi |
| 7,480,042 B1 | 1/2009 | Phillips et al. |
| 7,494,577 B2 | 2/2009 | Williams et al. |
| 7,494,770 B2 | 2/2009 | Wilding et al. |
| 7,514,046 B2 | 4/2009 | Kechagia et al. |
| 7,518,726 B2 | 4/2009 | Rulison et al. |
| 7,521,186 B2 | 4/2009 | Burd Mehta |
| 7,527,769 B2 | 5/2009 | Bunch et al. |
| D595,423 S | 6/2009 | Johansson et al. |
| 7,553,671 B2 | 6/2009 | Sinclair et al. |
| D596,312 S | 7/2009 | Giraud et al. |
| D598,566 S | 8/2009 | Allaer |
| D599,234 S | 9/2009 | Ito |
| 7,595,197 B2 | 9/2009 | Brasseur |
| 7,604,938 B2 | 10/2009 | Takahashi et al. |
| 7,635,588 B2 | 12/2009 | King et al. |
| 7,645,581 B2 | 1/2010 | Knapp et al. |
| 7,670,559 B2 | 3/2010 | Chien et al. |
| 7,674,431 B2 | 3/2010 | Ganesan |
| 7,689,022 B2 | 3/2010 | Weiner et al. |
| 7,704,735 B2 | 4/2010 | Facer et al. |
| 7,723,123 B1 | 5/2010 | Murphy et al. |
| D618,820 S | 6/2010 | Wilson et al. |
| 7,727,371 B2 | 6/2010 | Kennedy et al. |
| 7,727,477 B2 | 6/2010 | Boronkay et al. |
| 7,744,817 B2 | 6/2010 | Bui |
| D621,060 S | 8/2010 | Handique |
| D628,305 S | 11/2010 | Gorrec et al. |
| 7,867,776 B2 | 1/2011 | Kennedy et al. |
| D632,799 S | 2/2011 | Canner et al. |
| 7,892,819 B2 | 2/2011 | Wilding et al. |
| D637,737 S | 5/2011 | Wilson et al. |
| 7,955,864 B2 | 6/2011 | Cox et al. |
| 7,998,708 B2 | 8/2011 | Handique et al. |
| 8,071,056 B2 | 12/2011 | Burns et al. |
| 8,088,616 B2 | 1/2012 | Handique |
| 8,105,783 B2 | 1/2012 | Handique |
| 8,110,158 B2 | 2/2012 | Handique |
| 8,133,671 B2 | 3/2012 | Williams et al. |
| 8,182,763 B2 | 5/2012 | Duffy et al. |
| 8,246,919 B2 | 8/2012 | Herchenbach et al. |
| 8,273,308 B2 | 9/2012 | Handique et al. |
| D669,597 S | 10/2012 | Cavada et al. |
| 8,287,820 B2 | 10/2012 | Williams et al. |
| 8,323,584 B2 | 12/2012 | Ganesan |
| 8,323,900 B2 | 12/2012 | Handique et al. |
| 8,324,372 B2 | 12/2012 | Brahmasandra et al. |
| 8,415,103 B2 | 4/2013 | Handique |
| 8,420,015 B2 | 4/2013 | Ganesan et al. |
| 8,440,149 B2 | 5/2013 | Handique |
| 8,470,586 B2 | 6/2013 | Wu et al. |
| 8,473,104 B2 | 6/2013 | Handique et al. |
| D686,749 S | 7/2013 | Trump |
| D687,567 S | 8/2013 | Jungheim et al. |
| D692,162 S | 10/2013 | Lentz et al. |
| 8,679,831 B2 | 3/2014 | Handique et al. |
| D702,854 S | 4/2014 | Nakahana et al. |
| 8,685,341 B2 | 4/2014 | Ganesan |
| 8,703,069 B2 | 4/2014 | Handique et al. |
| 8,709,787 B2 | 4/2014 | Handique |
| 8,710,211 B2 | 4/2014 | Brahmasandra et al. |
| 8,734,733 B2 | 5/2014 | Handique |
| D710,024 S | 7/2014 | Guo |
| 8,765,076 B2 | 7/2014 | Handique et al. |
| 8,852,862 B2 | 10/2014 | Wu et al. |
| 8,883,490 B2 | 11/2014 | Handique et al. |
| 8,894,947 B2 | 11/2014 | Ganesan et al. |
| 8,895,311 B1 | 11/2014 | Handique et al. |
| D729,404 S | 5/2015 | Teich et al. |
| 9,028,773 B2 | 5/2015 | Ganesan |
| 9,040,288 B2 | 5/2015 | Handique et al. |
| 9,051,604 B2 | 6/2015 | Handique |
| 9,080,207 B2 | 7/2015 | Handique et al. |
| D742,027 S | 10/2015 | Lentz et al. |
| 9,186,677 B2 | 11/2015 | Williams et al. |
| 9,217,143 B2 | 12/2015 | Brahmasandra et al. |
| 9,222,954 B2 | 12/2015 | Lentz et al. |
| 9,238,223 B2 | 1/2016 | Handique |
| 9,259,734 B2 | 2/2016 | Williams et al. |
| 9,259,735 B2 | 2/2016 | Handique et al. |
| 9,347,586 B2 | 5/2016 | Williams et al. |
| 9,480,983 B2 | 11/2016 | Lentz et al. |
| 9,528,142 B2 | 12/2016 | Handique |
| 9,618,139 B2 | 4/2017 | Handique |
| D787,087 S | 6/2017 | Duffy et al. |
| 9,670,528 B2 | 6/2017 | Handique et al. |
| 9,677,121 B2 | 6/2017 | Ganesan et al. |
| 9,701,957 B2 | 7/2017 | Wilson et al. |
| 9,745,623 B2 | 8/2017 | Steel |
| 9,765,389 B2 | 9/2017 | Gubatayao et al. |
| 9,802,199 B2 | 10/2017 | Handique et al. |
| 9,815,057 B2 | 11/2017 | Handique |
| 2001/0005489 A1 | 6/2001 | Roach et al. |
| 2001/0012492 A1 | 8/2001 | Acosta et al. |
| 2001/0016358 A1 | 8/2001 | Osawa et al. |
| 2001/0021355 A1 | 9/2001 | Baugh et al. |
| 2001/0023848 A1 | 9/2001 | Gjerde et al. |
| 2001/0038450 A1 | 11/2001 | McCaffrey et al. |
| 2001/0045358 A1 | 11/2001 | Kopf-Sill et al. |
| 2001/0046702 A1 | 11/2001 | Schembri |
| 2001/0048899 A1 | 12/2001 | Marouiss et al. |
| 2001/0055765 A1 | 12/2001 | O'Keefe et al. |
| 2002/0001848 A1 | 1/2002 | Bedingham et al. |
| 2002/0008053 A1 | 1/2002 | Hansen et al. |
| 2002/0009015 A1 | 1/2002 | Laugharn, Jr. et al. |
| 2002/0014443 A1 | 2/2002 | Hansen et al. |
| 2002/0015667 A1 | 2/2002 | Chow |
| 2002/0021983 A1 | 2/2002 | Comte et al. |
| 2002/0022261 A1 | 2/2002 | Anderson et al. |
| 2002/0037499 A1 | 3/2002 | Quake et al. |
| 2002/0039783 A1 | 4/2002 | McMillan et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0058332 A1 | 5/2002 | Quake et al. |
| 2002/0060156 A1 | 5/2002 | Mathies et al. |
| 2002/0068357 A1 | 6/2002 | Mathies et al. |
| 2002/0068821 A1 | 6/2002 | Gundling |
| 2002/0090320 A1 | 7/2002 | Burow et al. |
| 2002/0094303 A1 | 7/2002 | Yamamoto et al. |
| 2002/0131903 A1 | 9/2002 | Ingenhoven et al. |
| 2002/0141903 A1 | 10/2002 | Parunak et al. |
| 2002/0142471 A1 | 10/2002 | Handique et al. |
| 2002/0143297 A1 | 10/2002 | Francavilla et al. |
| 2002/0143437 A1 | 10/2002 | Handique et al. |

(56) References Cited

U.S. PATENT DOCUMENTS

| | | |
|---|---|---|
| 2002/0155010 A1 | 10/2002 | Karp et al. |
| 2002/0155477 A1 | 10/2002 | Ito |
| 2002/0169518 A1 | 11/2002 | Luoma et al. |
| 2002/0187557 A1 | 12/2002 | Hobbs et al. |
| 2002/0192808 A1 | 12/2002 | Gambini et al. |
| 2003/0008308 A1 | 1/2003 | Enzelberger et al. |
| 2003/0019522 A1 | 1/2003 | Parunak |
| 2003/0022392 A1 | 1/2003 | Hudak |
| 2003/0049174 A1 | 3/2003 | Ganesan |
| 2003/0049833 A1 | 3/2003 | Chen et al. |
| 2003/0059823 A1 | 3/2003 | Matsunaga et al. |
| 2003/0064507 A1 | 4/2003 | Gallagher et al. |
| 2003/0070677 A1 | 4/2003 | Handique et al. |
| 2003/0072683 A1 | 4/2003 | Stewart et al. |
| 2003/0073106 A1 | 4/2003 | Johansen et al. |
| 2003/0083686 A1 | 5/2003 | Freeman et al. |
| 2003/0087300 A1 | 5/2003 | Knapp et al. |
| 2003/0096310 A1 | 5/2003 | Hansen et al. |
| 2003/0099954 A1 | 5/2003 | Miltenyi et al. |
| 2003/0127327 A1 | 7/2003 | Kurnik |
| 2003/0136679 A1 | 7/2003 | Bohn et al. |
| 2003/0156991 A1 | 8/2003 | Halas et al. |
| 2003/0186295 A1 | 10/2003 | Colin et al. |
| 2003/0190608 A1 | 10/2003 | Blackburn et al. |
| 2003/0199081 A1 | 10/2003 | Wilding et al. |
| 2003/0211517 A1 | 11/2003 | Carulli et al. |
| 2004/0014202 A1 | 1/2004 | King et al. |
| 2004/0014238 A1 | 1/2004 | Krug et al. |
| 2004/0018116 A1 | 1/2004 | Desmond et al. |
| 2004/0018119 A1 | 1/2004 | Massaro |
| 2004/0022689 A1 | 2/2004 | Wulf et al. |
| 2004/0029258 A1 | 2/2004 | Heaney et al. |
| 2004/0029260 A1 | 2/2004 | Hansen et al. |
| 2004/0037739 A1 | 2/2004 | McNeely et al. |
| 2004/0053290 A1 | 3/2004 | Terbrueggen et al. |
| 2004/0063217 A1 | 4/2004 | Webster et al. |
| 2004/0065655 A1 | 4/2004 | Brown |
| 2004/0072278 A1 | 4/2004 | Chou et al. |
| 2004/0072375 A1 | 4/2004 | Gjerde et al. |
| 2004/0086427 A1 | 5/2004 | Childers et al. |
| 2004/0086956 A1 | 5/2004 | Bachur |
| 2004/0132059 A1 | 7/2004 | Scurati et al. |
| 2004/0141887 A1 | 7/2004 | Mainquist et al. |
| 2004/0151629 A1 | 8/2004 | Pease et al. |
| 2004/0157220 A1 | 8/2004 | Kurnool et al. |
| 2004/0161788 A1 | 8/2004 | Chen et al. |
| 2004/0189311 A1 | 9/2004 | Glezer et al. |
| 2004/0197810 A1 | 10/2004 | Takenaka et al. |
| 2004/0200909 A1 | 10/2004 | McMillan et al. |
| 2004/0209331 A1 | 10/2004 | Ririe |
| 2004/0209354 A1 | 10/2004 | Mathies et al. |
| 2004/0219070 A1 | 11/2004 | Handique |
| 2004/0224317 A1 | 11/2004 | Kordunsky et al. |
| 2004/0235154 A1 | 11/2004 | Oh et al. |
| 2004/0240097 A1 | 12/2004 | Evans |
| 2005/0009174 A1 | 1/2005 | Nikiforov et al. |
| 2005/0013737 A1 | 1/2005 | Chow et al. |
| 2005/0037471 A1 | 2/2005 | Liu et al. |
| 2005/0041525 A1 | 2/2005 | Pugia et al. |
| 2005/0042639 A1 | 2/2005 | Knapp et al. |
| 2005/0048540 A1 | 3/2005 | Inami et al. |
| 2005/0058574 A1 | 3/2005 | Bysouth et al. |
| 2005/0058577 A1 | 3/2005 | Micklash et al. |
| 2005/0064535 A1 | 3/2005 | Favuzzi et al. |
| 2005/0069898 A1 | 3/2005 | Moon et al. |
| 2005/0084424 A1 | 4/2005 | Ganesan et al. |
| 2005/0106066 A1 | 5/2005 | Saltsman et al. |
| 2005/0112754 A1 | 5/2005 | Yoon et al. |
| 2005/0121324 A1 | 6/2005 | Park et al. |
| 2005/0129580 A1 | 6/2005 | Swinehart et al. |
| 2005/0133370 A1 | 6/2005 | Park et al. |
| 2005/0135655 A1 | 6/2005 | Kopf-sill et al. |
| 2005/0142036 A1 | 6/2005 | Kim et al. |
| 2005/0152808 A1 | 7/2005 | Ganesan |
| 2005/0158781 A1 | 7/2005 | Woudenberg et al. |
| 2005/0170362 A1 | 8/2005 | Wada et al. |
| 2005/0186585 A1 | 8/2005 | Juncosa et al. |
| 2005/0196321 A1 | 9/2005 | Huang |
| 2005/0202470 A1 | 9/2005 | Sundberg et al. |
| 2005/0202489 A1 | 9/2005 | Cho et al. |
| 2005/0202504 A1 | 9/2005 | Anderson et al. |
| 2005/0208676 A1 | 9/2005 | Kahatt |
| 2005/0214172 A1 | 9/2005 | Burgisser |
| 2005/0220675 A1 | 10/2005 | Reed et al. |
| 2005/0227269 A1 | 10/2005 | Lloyd et al. |
| 2005/0233370 A1 | 10/2005 | Ammann et al. |
| 2005/0238545 A1 | 10/2005 | Parce et al. |
| 2005/0272079 A1 | 12/2005 | Burns et al. |
| 2005/0276728 A1 | 12/2005 | Muller-Cohn et al. |
| 2006/0041058 A1 | 2/2006 | Yin et al. |
| 2006/0057039 A1 | 3/2006 | Morse et al. |
| 2006/0057629 A1 | 3/2006 | Kim |
| 2006/0062696 A1 | 3/2006 | Chow et al. |
| 2006/0094108 A1 | 5/2006 | Yoder et al. |
| 2006/0113190 A1 | 6/2006 | Kurnik |
| 2006/0133965 A1 | 6/2006 | Tajima et al. |
| 2006/0134790 A1 | 6/2006 | Tanaka et al. |
| 2006/0148063 A1 | 7/2006 | Fauzzi et al. |
| 2006/0165558 A1 | 7/2006 | Witty et al. |
| 2006/0165559 A1 | 7/2006 | Greenstein et al. |
| 2006/0166233 A1 | 7/2006 | Wu et al. |
| 2006/0177376 A1 | 8/2006 | Tomalia et al. |
| 2006/0177855 A1 | 8/2006 | Utermohlen et al. |
| 2006/0183216 A1 | 8/2006 | Handique |
| 2006/0201887 A1 | 9/2006 | Siddiqi |
| 2006/0205085 A1 | 9/2006 | Handique |
| 2006/0207944 A1 | 9/2006 | Siddiqi |
| 2006/0210435 A1 | 9/2006 | Alavie et al. |
| 2006/0223169 A1 | 10/2006 | Bedingham et al. |
| 2006/0228734 A1 | 10/2006 | Vann et al. |
| 2006/0246493 A1 | 11/2006 | Jensen et al. |
| 2006/0246533 A1 | 11/2006 | Fathollahi et al. |
| 2006/0269641 A1 | 11/2006 | Atwood et al. |
| 2006/0269961 A1 | 11/2006 | Fukushima et al. |
| 2007/0004028 A1 | 1/2007 | Lair et al. |
| 2007/0009386 A1 | 1/2007 | Padmanabhan et al. |
| 2007/0020699 A1 | 1/2007 | Carpenter et al. |
| 2007/0020764 A1 | 1/2007 | Miller |
| 2007/0026421 A1 | 2/2007 | Sundberg et al. |
| 2007/0042441 A1 | 2/2007 | Masters et al. |
| 2007/0048188 A1 | 3/2007 | Bigus |
| 2007/0054413 A1 | 3/2007 | Aviles et al. |
| 2007/0077648 A1 | 4/2007 | Okamoto et al. |
| 2007/0092901 A1 | 4/2007 | Ligler et al. |
| 2007/0098600 A1 | 5/2007 | Kayyem et al. |
| 2007/0099200 A1 | 5/2007 | Chow et al. |
| 2007/0104617 A1 | 5/2007 | Coulling et al. |
| 2007/0116613 A1 | 5/2007 | Elsener |
| 2007/0154895 A1 | 7/2007 | Spaid et al. |
| 2007/0177147 A1 | 8/2007 | Parce |
| 2007/0178607 A1 | 8/2007 | Prober et al. |
| 2007/0184463 A1 | 8/2007 | Molho et al. |
| 2007/0184547 A1 | 8/2007 | Handique et al. |
| 2007/0196237 A1 | 8/2007 | Neuzil et al. |
| 2007/0196238 A1 | 8/2007 | Kennedy et al. |
| 2007/0199821 A1 | 8/2007 | Chow |
| 2007/0215554 A1 | 9/2007 | Kreuwel et al. |
| 2007/0218459 A1 | 9/2007 | Miller et al. |
| 2007/0231213 A1 | 10/2007 | Prabhu et al. |
| 2007/0243626 A1 | 10/2007 | Windeyer et al. |
| 2007/0261479 A1 | 11/2007 | Spaid et al. |
| 2007/0269861 A1 | 11/2007 | Williams et al. |
| 2007/0292941 A1 | 12/2007 | Handique et al. |
| 2008/0000774 A1 | 1/2008 | Park et al. |
| 2008/0003649 A1 | 1/2008 | Maltezos et al. |
| 2008/0017306 A1 | 1/2008 | Liu et al. |
| 2008/0050804 A1 | 2/2008 | Handique et al. |
| 2008/0056948 A1 | 3/2008 | Dale et al. |
| 2008/0069729 A1 | 3/2008 | McNeely |
| 2008/0075634 A1 | 3/2008 | Herchenbach et al. |
| 2008/0090244 A1 | 4/2008 | Knapp et al. |
| 2008/0095673 A1 | 4/2008 | Xu |
| 2008/0118987 A1 | 5/2008 | Eastwood et al. |
| 2008/0124723 A1 | 5/2008 | Dale et al. |

(56) References Cited

U.S. PATENT DOCUMENTS

| | | |
|---|---|---|
| 2008/0149840 A1 | 6/2008 | Handique et al. |
| 2008/0160601 A1 | 7/2008 | Handique |
| 2008/0176230 A1 | 7/2008 | Owen et al. |
| 2008/0182301 A1 | 7/2008 | Handique et al. |
| 2008/0192254 A1 | 8/2008 | Kim et al. |
| 2008/0226502 A1 | 9/2008 | Jonsmann et al. |
| 2008/0240898 A1 | 10/2008 | Manz et al. |
| 2008/0247914 A1 | 10/2008 | Edens et al. |
| 2008/0262213 A1 | 10/2008 | Wu et al. |
| 2008/0280285 A1 | 11/2008 | Chen et al. |
| 2008/0308500 A1 | 12/2008 | Brassard |
| 2009/0047180 A1 | 2/2009 | Kawahara |
| 2009/0047713 A1 | 2/2009 | Handique |
| 2009/0066339 A1 | 3/2009 | Glezer et al. |
| 2009/0129978 A1 | 5/2009 | Wilson et al. |
| 2009/0130719 A1 | 5/2009 | Handique |
| 2009/0130745 A1 | 5/2009 | Williams et al. |
| 2009/0131650 A1 | 5/2009 | Brahmasandra et al. |
| 2009/0134069 A1 | 5/2009 | Handique |
| 2009/0136385 A1 | 5/2009 | Handique et al. |
| 2009/0136386 A1 | 5/2009 | Duffy et al. |
| 2009/0155123 A1 | 6/2009 | Williams et al. |
| 2009/0189089 A1 | 7/2009 | Bedingham et al. |
| 2009/0221059 A1 | 9/2009 | Williams et al. |
| 2009/0223925 A1 | 9/2009 | Morse et al. |
| 2009/0325164 A1 | 12/2009 | Vossenaar et al. |
| 2010/0009351 A1 | 1/2010 | Brahmasandra et al. |
| 2010/0120129 A1 | 5/2010 | Amshey et al. |
| 2010/0173393 A1 | 7/2010 | Handique et al. |
| 2010/0284864 A1 | 11/2010 | Holenstein et al. |
| 2011/0008825 A1 | 1/2011 | Ingber et al. |
| 2011/0027151 A1 | 2/2011 | Handique et al. |
| 2011/0097493 A1 | 4/2011 | Kerr et al. |
| 2011/0127292 A1 | 6/2011 | Sarofim et al. |
| 2011/0158865 A1 | 6/2011 | Miller et al. |
| 2011/0207140 A1 | 8/2011 | Handique et al. |
| 2011/0210257 A9 | 9/2011 | Handique et al. |
| 2011/0287447 A1 | 11/2011 | Norderhaug |
| 2011/0300033 A1 | 12/2011 | Battisti |
| 2012/0022695 A1 | 1/2012 | Handique et al. |
| 2012/0085416 A1 | 4/2012 | Ganesan |
| 2012/0122108 A1 | 5/2012 | Handique |
| 2012/0122231 A1 | 5/2012 | Tajima |
| 2012/0160826 A1 | 6/2012 | Handique |
| 2012/0171678 A1 | 7/2012 | Maltezos et al. |
| 2012/0171759 A1 | 7/2012 | Williams et al. |
| 2012/0183454 A1 | 7/2012 | Handique |
| 2012/0258463 A1 | 10/2012 | Duffy et al. |
| 2013/0037564 A1 | 2/2013 | Williams et al. |
| 2013/0071851 A1 | 3/2013 | Handique et al. |
| 2013/0096292 A1 | 4/2013 | Brahmasandra et al. |
| 2013/0101990 A1 | 4/2013 | Handique et al. |
| 2013/0164832 A1 | 6/2013 | Ganesan et al. |
| 2013/0183769 A1 | 7/2013 | Tajima |
| 2013/0217013 A1 | 8/2013 | Steel et al. |
| 2013/0217102 A1 | 8/2013 | Ganesan et al. |
| 2013/0251602 A1 | 9/2013 | Handique et al. |
| 2013/0280131 A1 | 10/2013 | Handique et al. |
| 2013/0288358 A1 | 10/2013 | Handique et al. |
| 2013/0315800 A1 | 11/2013 | Yin et al. |
| 2014/0030798 A1 | 1/2014 | Wu et al. |
| 2014/0045186 A1 | 2/2014 | Gubatayao et al. |
| 2014/0206088 A1 | 7/2014 | Lentz et al. |
| 2014/0212882 A1 | 7/2014 | Handique et al. |
| 2014/0227710 A1 | 8/2014 | Handique et al. |
| 2014/0297047 A1 | 10/2014 | Ganesan et al. |
| 2014/0323357 A1 | 10/2014 | Handique et al. |
| 2014/0323711 A1 | 10/2014 | Brahmasandra et al. |
| 2014/0329301 A1 | 11/2014 | Handique et al. |
| 2014/0342352 A1 | 11/2014 | Handique et al. |
| 2014/0377850 A1 | 12/2014 | Handique et al. |
| 2015/0064702 A1 | 3/2015 | Handique et al. |
| 2015/0118684 A1 | 4/2015 | Wu et al. |
| 2015/0133345 A1 | 5/2015 | Handique et al. |
| 2015/0142186 A1 | 5/2015 | Handique et al. |
| 2015/0152477 A1 | 6/2015 | Ganesan et al. |
| 2015/0174579 A1 | 6/2015 | Iten et al. |
| 2015/0315631 A1 | 11/2015 | Handique et al. |
| 2015/0328638 A1 | 11/2015 | Handique et al. |
| 2015/0376682 A1 | 12/2015 | Handique |
| 2016/0038942 A1 | 2/2016 | Roberts |
| 2016/0102305 A1 | 4/2016 | Brahmasandra et al. |
| 2016/0107161 A1 | 4/2016 | Lentz et al. |
| 2016/0250635 A1 | 9/2016 | Handique |
| 2016/0250640 A1 | 9/2016 | Williams et al. |
| 2016/0333337 A1 | 11/2016 | Duffy et al. |
| 2017/0097373 A1 | 4/2017 | Williams et al. |
| 2017/0266666 A1 | 9/2017 | Lentz et al. |
| 2018/0112252 A1 | 4/2018 | Handique |
| 2018/0119204 A1 | 5/2018 | Ganesan et al. |

FOREIGN PATENT DOCUMENTS

| | | |
|---|---|---|
| CN | 101466848 | 6/2009 |
| CN | 101522909 | 9/2009 |
| CN | 103540518 | 1/2014 |
| DE | 19929734 | 12/1999 |
| DE | 19833293 C1 | 1/2000 |
| EP | 0365828 A2 | 5/1990 |
| EP | 0483620 A2 | 5/1992 |
| EP | 0688602 A2 | 12/1995 |
| EP | 0766256 | 4/1997 |
| EP | 0772494 B1 | 5/1997 |
| EP | 1059458 A2 | 12/2000 |
| EP | 1077086 A2 | 2/2001 |
| EP | 1346772 A2 | 9/2003 |
| EP | 1541237 A2 | 6/2005 |
| EP | 1574586 A2 | 9/2005 |
| EP | 1745153 | 1/2007 |
| EP | 1780290 A2 | 5/2007 |
| EP | 1792656 A1 | 6/2007 |
| EP | 2372367 A1 | 10/2011 |
| FR | 2672301 | 8/1992 |
| FR | 2795426 | 12/2000 |
| GB | 2453432 A | 4/2009 |
| JP | S50-100881 | 8/1975 |
| JP | 58212921 A | 12/1983 |
| JP | S62-119460 | 5/1987 |
| JP | H01-502319 | 8/1989 |
| JP | H 03181853 | 8/1991 |
| JP | 04-053555 U | 5/1992 |
| JP | 06-064156 U | 9/1994 |
| JP | 07-020010 | 1/1995 |
| JP | H07-290706 | 11/1995 |
| JP | H08-122336 | 5/1996 |
| JP | H08-173194 | 7/1996 |
| JP | H08-211071 | 8/1996 |
| JP | H08-285859 | 11/1996 |
| JP | H09-325151 | 12/1997 |
| JP | 2001-502790 | 1/1998 |
| JP | 11009258 | 1/1999 |
| JP | H 11-501504 | 2/1999 |
| JP | H11-503315 | 3/1999 |
| JP | 2000-514928 | 4/1999 |
| JP | H11-156231 | 6/1999 |
| JP | H11-316226 | 11/1999 |
| JP | H11-515106 | 12/1999 |
| JP | 2000-180455 | 6/2000 |
| JP | 2000-266760 | 9/2000 |
| JP | 2000-275255 | 10/2000 |
| JP | 2001-502319 | 2/2001 |
| JP | 2001-204462 | 7/2001 |
| JP | 2001-509437 | 7/2001 |
| JP | 3191150 B2 | 7/2001 |
| JP | 2001-515216 | 9/2001 |
| JP | 2001-523812 | 11/2001 |
| JP | 2001-527220 | 12/2001 |
| JP | 2002-503331 | 1/2002 |
| JP | 2002-085961 | 3/2002 |
| JP | 2002-517735 | 6/2002 |
| JP | 2002-215241 | 7/2002 |
| JP | 2002-540382 | 11/2002 |
| JP | 2002-544476 | 12/2002 |
| JP | 2003-500674 | 1/2003 |

(56) References Cited

FOREIGN PATENT DOCUMENTS

| | | |
|---|---|---|
| JP | 2003-047839 A | 2/2003 |
| JP | 2003-047840 A | 2/2003 |
| JP | 2003-516125 | 5/2003 |
| JP | 2003-164279 | 6/2003 |
| JP | 2003-185584 | 7/2003 |
| JP | 2003-299485 | 10/2003 |
| JP | 2003-329693 | 11/2003 |
| JP | 2003-329696 | 11/2003 |
| JP | 2003-532382 A | 11/2003 |
| JP | 2004-003989 | 1/2004 |
| JP | 2004-506179 A | 2/2004 |
| JP | 2004-150797 A | 5/2004 |
| JP | 2004-531360 A | 10/2004 |
| JP | 2004-533838 | 11/2004 |
| JP | 2004-361421 | 12/2004 |
| JP | 2004-536291 | 12/2004 |
| JP | 2004-536689 A | 12/2004 |
| JP | 2005-009870 | 1/2005 |
| JP | 2005-010179 | 1/2005 |
| JP | 2005-511264 | 4/2005 |
| JP | 2005-514718 | 5/2005 |
| JP | 2005-518825 | 6/2005 |
| JP | 2005-176613 A | 7/2005 |
| JP | 2005-192439 | 7/2005 |
| JP | 2005-192554 | 7/2005 |
| JP | 2005-204661 | 8/2005 |
| JP | 2005-525816 | 9/2005 |
| JP | 2005-291954 A | 10/2005 |
| JP | 2005-532043 | 10/2005 |
| JP | 2005-323519 | 11/2005 |
| JP | 2005-533652 | 11/2005 |
| JP | 2005-535904 | 11/2005 |
| JP | 2006-021156 A | 1/2006 |
| JP | 2006-094866 A | 4/2006 |
| JP | 2006-145458 | 6/2006 |
| JP | 2006-167569 | 6/2006 |
| JP | 2006-284409 | 10/2006 |
| JP | 2007-074960 | 3/2007 |
| JP | 2007-097477 | 4/2007 |
| JP | 2007-101364 | 4/2007 |
| JP | 2007-510518 | 4/2007 |
| JP | 2007-514405 A | 6/2007 |
| JP | 2007-178328 | 7/2007 |
| JP | 2007-535933 | 12/2007 |
| JP | 2009-515140 | 4/2009 |
| JP | 2009-542207 | 12/2009 |
| RU | 2418633 | 5/2011 |
| WO | WO 1988/006633 | 9/1988 |
| WO | WO 1990/012350 | 10/1990 |
| WO | WO 1992/005443 | 4/1992 |
| WO | WO 1994/011103 | 5/1994 |
| WO | WO 1996/004547 | 2/1996 |
| WO | WO 1996/018731 | 6/1996 |
| WO | WO 1997/005492 | 2/1997 |
| WO | WO 1997/021090 | 6/1997 |
| WO | WO 1998/000231 | 1/1998 |
| WO | WO 1998/022625 | 5/1998 |
| WO | WO 1998/35013 A1 | 8/1998 |
| WO | WO 1998/049548 | 11/1998 |
| WO | WO 1998/053311 | 11/1998 |
| WO | WO 1999/001688 | 1/1999 |
| WO | WO 1999/009042 | 2/1999 |
| WO | WO 1999/012016 | 3/1999 |
| WO | WO 1999/017093 | 4/1999 |
| WO | WO 1999/029703 | 6/1999 |
| WO | WO 1999/033559 | 7/1999 |
| WO | WO 2001/005510 | 1/2001 |
| WO | WO 2001/014931 | 3/2001 |
| WO | WO 2001/027614 | 4/2001 |
| WO | WO 2001/028684 | 4/2001 |
| WO | WO 2001/030995 | 5/2001 |
| WO | WO 2001/041931 | 6/2001 |
| WO | WO 2001/054813 | 8/2001 |
| WO | WO 2001/089681 | 11/2001 |
| WO | WO 2002/048164 | 6/2002 |
| WO | WO 2002/072264 | 9/2002 |
| WO | WO 2002/078845 | 10/2002 |
| WO | WO 2002/086454 | 10/2002 |
| WO | WO 2003/007677 | 1/2003 |
| WO | WO 2003/012325 | 2/2003 |
| WO | WO 2003/012406 | 2/2003 |
| WO | WO 2003/048295 | 6/2003 |
| WO | WO 2003/055605 | 7/2003 |
| WO | WO 2003/076661 | 9/2003 |
| WO | WO 2003/087410 | 10/2003 |
| WO | WO 2004/007081 | 1/2004 |
| WO | WO 2004/048545 | 6/2004 |
| WO | WO 2004/055522 | 7/2004 |
| WO | WO 2004/056485 | 7/2004 |
| WO | WO 2004/074848 | 9/2004 |
| WO | WO 2004/094986 | 11/2004 |
| WO | WO 2005/008255 | 1/2005 |
| WO | WO 2005/011867 | 2/2005 |
| WO | WO 2005/030984 | 4/2005 |
| WO | WO 2005/072353 | 8/2005 |
| WO | WO 2005/107947 | 11/2005 |
| WO | WO 2005/108571 | 11/2005 |
| WO | WO 2005/108620 | 11/2005 |
| WO | WO 2005/116202 | 12/2005 |
| WO | WO 2005/118867 | 12/2005 |
| WO | WO 2005/120710 | 12/2005 |
| WO | WO 2006/010584 | 2/2006 |
| WO | WO 2006/032044 | 3/2006 |
| WO | WO 2006/035800 | 4/2006 |
| WO | WO 2006/043642 | 4/2006 |
| WO | WO 2006/066001 | 6/2006 |
| WO | WO 2006/079082 | 7/2006 |
| WO | WO 2006/081995 | 8/2006 |
| WO | WO 2006/113198 | 10/2006 |
| WO | WO 2006/119280 | 11/2006 |
| WO | WO 2007/044917 | 4/2007 |
| WO | WO 2007/050327 | 5/2007 |
| WO | WO 2007/064117 | 6/2007 |
| WO | WO 2007/091530 | 8/2007 |
| WO | WO 2007/112114 | 10/2007 |
| WO | WO 2008/005321 | 1/2008 |
| WO | WO 2008/030914 | 3/2008 |
| WO | WO 2008/060604 | 5/2008 |
| WO | WO 2009/012185 | 1/2009 |
| WO | WO 2009/054870 | 4/2009 |
| WO | WO 2010/118541 | 10/2010 |
| WO | WO 2010/130310 | 11/2010 |
| WO | WO 2010/140680 | 12/2010 |
| WO | WO 2011/101467 | 8/2011 |

OTHER PUBLICATIONS

Allemand et al., "pH-Dependent Specific Binding and Combing of DNA", Biophys J. (1997) 73(4): 2064-2070.

Bollet, C. et al., "A simple method for the isolation of chromosomal DNA from Gram positive or acid-fast bacteria", Nucleic Acids Research, vol. 19, No. 8 (1991), p. 1955.

Brahmasandra et al., On-chip DNA detection in microfabricated separation systems, SPIE Conference on Microfluidic Devices and Systems, 1998, vol. 3515, pp. 242-251, Santa Clara, CA.

Breadmore, M.C. et al., "Microchip-Based Purification of DNA from Biological Samples", Anal. Chem., vol. 75 (2003), pp. 1880-1886.

Brody, et al., Diffusion-Based Extraction in a Microfabricated Device, Sensors and Actuators Elsevier, 1997, vol. A58, No. 1, pp. 13-18.

Broyles et al., "Sample Filtration, Concentration, and Separation Integrated on Microfluidic Devices" Analytical Chemistry (American Chemical Society), (2003) 75(11): 2761-2767.

Burns et al., "An Integrated Nanoliter DNA Analysis Device", Science 282:484-487 (1998).

Carlen et al., "Paraffin Actuated Surface Micromachined Valve," in IEEE MEMS 2000 Conference, Miyazaki, Japan, (Jan. 2000) pp. 381-385.

Chung, Y. et al., "Microfluidic chip for high efficiency DNA extraction", Miniaturisation for Chemistry, Biology & Bioengineering, vol. 4, No. 2 (Apr. 2004), pp. 141-147.

(56) References Cited

OTHER PUBLICATIONS

European Supplemental Search Report dated Aug. 5, 2010 for Application No. EP 08826342.1, filed Jul. 11, 2008.
European Supplemental Search Report dated Jul. 13, 2012 for Application No. EP 08843060.8, filed Jul. 14, 2008.
Goldmeyer et al., "Identification of *Staphylococcus aureus* and Determination of Methicillin Resistance Directly from Positive Blood Cultures by Isothermal Amplification and a Disposable Detection Device", J Clin Microbial. (Apr. 2008) 46(4): 1534-1536.
Handique et al, "Microfluidic flow control using selective hydrophobic patterning", SPIE, (1997) 3224: 185-194.
Handique et al., "On-Chip Thermopneumatic Pressure for Discrete Drop Pumping", Anal. Chem., (2001) 73(8):1831-1838.
Handique et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.
Handique et al., "Mathematical Modeling of Drop Mixing in a Slit-Type Microchannel", J. Micromech. Microeng., 11:548-554 (2001).
Handique et al., "Nanoliter Liquid Metering in Microchannels Using Hydrophobic Patterns", Anal. Chem., 72(17):4100-4109 (2000).
Harding et al., "DNA isolation using Methidium-Spermine-Sepharose", Meth Enzymol. (1992) 216: 29-39.
Harding et al., "Rapid isolation of DNA from complex biological samples using a novel capture reagent—methidium-sperminesepharose", Nucl Acids Res. (1989) 17(17): 6947-6958.
He, et al., Microfabricated Filters for Microfluidic Analytical Systems, Analytical Chemistry, American Chemical Society, 1999, vol. 71, No. 7, pp. 1464-1468.
Ibrahim, et al., Real-Time Microchip PCR for Detecting Single-Base Differences in Viral and Human DNA, Analytical Chemistry, American Chemical Society, 1998, 70(9): 2013-2017.
International Preliminary Report on Patentability and Written Opinion dated Jan. 19, 2010 for Application No. PCT/US2008/008640, filed Jul. 14, 2008.
International Preliminary Report on Patentability dated Jan. 19, 2010 for Application No. PCT/US2008/069897, filed Jul. 11, 2008.
International Search Report and Written Opinion dated Apr. 4, 2008 for PCT/US2007/007513, filed Mar. 26, 2007.
International Search Report and Written Opinion, dated Oct. 3, 2008, issued in International Application No. PCT/US2008/069897, filed Jul. 11, 2008.
International Search Report dated Jun. 17, 2009 for Application No. PCT/US2008/008640, filed Jul. 14, 2008.
Khandurina et al., Microfabricated Porous Membrane Structure for Sample Concentration and Electrophoretic Analysis, Analytical Chemistry American Chemical Society, 1999, 71(9): 1815-1819.
Kopp et al., Chemical Amplification: Continuous-Flow PCR on a Chip, www.sciencemag.org, 1998, vol. 280, pp. 1046-1048.
Kuo et al., "Remnant cationic dendrimers block RNA migration in electrophoresis after monophasic lysis", J Biotech. (2007) 129: 383-390.
Kutter et al., Solid Phase Extraction on Microfluidic Devices, J. Microcolumn Separations, John Wiley & Sons, Inc., 2000, 12(2): 93-97.
Labchem; Sodium Hydroxide, 0,5N (0.5M); Safety Data Sheet, 2015; 8 pages.
Lagally et al., Single-Molecule DNA Amplification and Analysis in an Integrated Microfluidic Device, Analytical Chemistry, American Chemical Society, 2001, 73(3): 565-570.
Livache et al., "Polypyrrole DNA chip on a Silicon Device: Example of Hepatitis C Virus Genotyping", Analytical Biochemistry, (1998) 255: 188-194.
Mascini et al., "DNA electrochemical biosensors", Fresenius J. Anal. Chem., 369: 15-22, (2001).
Meyers, R.A., Molecular Biology and Biotechnology: A Comprehensive Desk Reference; VCH Publishers, Inc. New York, NY; (1995) pp. 418-419.

Nakagawa et al., Fabrication of amino silane-coated microchip for DNA extraction from whole blood, J of Biotechnology, Mar. 2, 2005, 116: 105-111.
Northrup et al., A Miniature Analytical Instrument for Nucleic Acids Based on Micromachined Silicon Reaction Chambers, Analytical Chemistry, American Chemical Society, 1998, 70(5): 918-922.
Oh K.W. et al., "A Review of Microvalves", J Micromech Microeng. (2006) 16:R13-R39.
Oleschuk et al., Trapping of Bead-Based Reagents within Microfluidic Systems: On-Chip Solid-Phase Extraction and Electrochromatography, Analytical Chemistry, American Chemical Society, 2000, 72(3): 585-590.
Plambeck et al., "Electrochemical Studies of Antitumor Antibiotics", J. Electrochem Soc.: Electrochemical Science and Technology (1984), 131(11): 2556-2563.
Roche et al. "Ectodermal commitment of insulin-producing cells derived from mouse embryonic stem cells" Faseb J (2005) 19: 1341-1343.
Ross et al., Analysis of DNA Fragments from Conventional and Microfabricated PCR Devices Using Delayed Extraction MALDI-TOF Mass Spectrometry, Analytical Chemistry, American Chemical Society, 1998, 70(10): 2067-2073.
Sarma, K.S., "Liquid Crystal Displays", Chapter 32 in Electrical Measurement, Signal Processing, Displays, Jul. 15, 2003, ISBN: 978-0-8493-1733-0, Retrieved from the Internet: URL: http://http://197.14.51.10:81/pmb/ELECTRONIQUE/Electrical Measurement Signal Processing and Displays/Book/1733ch32.pdf; 21 pages.
Shoffner et al., Chip PCR.I. Surface Passivation of Microfabricated Silicon-Glass Chips for PCR, Nucleic Acids Research, Oxford University Press, (1996) 24(2): 375-379.
Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.
Tanaka et al., "Modification of DNA extraction from maize using polyamidoamine-dendrimer modified magnetic particles", Proceedings of the 74th Annual Meeting of the Electrochemical Society of Japan, Mar. 29, 2007; Faculty of Engineering, Science University of Tokyo; 2 pages.
Wang, "Survey and Summary, from DNA Biosensors to Gene Chips", Nucleic Acids Research, 28(16):3011-3016, (2000).
Waters et al., Microchip Device for Cell Lysis, Multiplex PCR Amplification, and Electrophoretic Sizing, Analytical Chemistry, American Chemical Society, 1998, 70(1): 158-162.
Weigl, et al., Microfluidic Diffusion-Based Separation and Detection, www.sciencemag.org, 1999, vol. 283, pp. 346-347.
Written Opinion (Rule 66) dated Oct. 24, 2013 for Application No. PCT/US2012/063091, filed Nov. 1, 2012.
Wu et al., "Polycationic dendrimers interact with RNA molecules: polyamine dendrimers inhibit the catalytic activity of Candida ribozymes", Chem Commun. (2005) 3: 313-315.
Yoza et al., "Fully Automated DNA Extraction from Blood Using Magnetic Particles Modified with a Hyperbranched Polyamidoamine Dendrimer", J Biosci Bioeng, 2003, 95(1): 21-26.
Yoza et al., DNA extraction using bacterial magnetic particles modified with hyperbranched polyamidoamine dendrimer, J Biotechnol., Mar. 20, 2003, 101(3): 219-228.
Zhou et al., "Cooperative binding and self-assembling behavior of cationic low molecular-weight dendrons with RNA molecules", Org Biomol Chem. (2006) 4(3): 581-585.
Zhou et al., "PAMAM dendrimers for efficient siRNA delivery and potent gene silencing", Chem Comm.(Camb.) (2006) 22: 2362-2364.
Cooley et al., "Applications of Ink-Jet Printing Technology to BioMEMS and Microfluidic Systems", Proceedings, SPIE Conference on Microfluids and BioMEMS, (Oct. 2001), 12 pages.
Kim et al., "Electrohydrodynamic Generation and Delivery of Monodisperse Picoliter Droplets Using a Poly(dimethylsiloxane) Microchip", Anal Chem. (2006) 78: 8011-8019.
Pal et al., "Phase Change Microvalve for Integrated Devices", Anal Chem. (2004) 76: 3740-3748.
European Extended Search Report dated Feb. 16, 2017 for Application No. EP 16191793.5, filed Sep. 30, 2016.

INTEGRATED HEATER AND MAGNETIC SEPARATOR

CLAIM OF PRIORITY

This application is a continuation of U.S. patent application Ser. No. 12/178,586, filed Jul. 23, 2008 and scheduled to issue as U.S. Pat. No. 9,618,139 on Apr. 11, 2017, which is a continuation-in-part of U.S. patent application Ser. No. 12/173,023, filed Jul. 14, 2008 and issued as U.S. Pat. No. 8,133,671 on Mar. 13, 2012, and U.S. patent application Ser. No. 12/218,498, filed Jul. 14, 2008 and issued as U.S. Pat. No. 9,186,677 on Nov. 17, 2015, both of which claim benefit of priority to U.S. Provisional Patent Application No. 60/959,437, filed Jul. 13, 2007, all of which are incorporated herein by reference in their entireties.

TECHNICAL FIELD

The technology described herein generally relates to an apparatus for providing thermal and magnetic energy to a receptacle containing a reaction mixture and a magnetic retention member. The technology more particularly relates to an apparatus for controlled heating of a reaction mixture, and for bringing about a separation of magnetic particles from the reaction mixture. The reaction mixture typically comprises polynucleotides from a biological sample that are being brought into a PCR-ready form.

BACKGROUND

The medical diagnostics industry is a critical element of today's healthcare infrastructure. At present, however, diagnostic analyses no matter how routine have become a bottleneck in patient care. There are several reasons for this. First, many diagnostic analyses can only be done with highly specialist equipment that is both expensive and only operable by trained clinicians. Such equipment is found in only a few locations—often just one in any given urban area. This means that most hospitals are required to send out samples for analyses to these locations, thereby incurring shipping costs and transportation delays, and possibly even sample loss or mishandling. Second, the equipment in question is typically not available 'on-demand' but instead runs in batches, thereby delaying the processing time for many samples because they must wait for a machine to fill up before they can be run.

Understanding that sample flow breaks down into several key steps, it would be desirable to consider ways to automate as many of these as possible. For example, a biological sample, once extracted from a patient, must be put in a form suitable for a processing regime that typically involves using PCR to amplify a vector of interest. Once amplified, the presence of a nucleotide of interest from the sample needs to be determined unambiguously. Preparing samples for PCR is currently a time-consuming and labor intensive step, though not one requiring specialist skills, and could usefully be automated. By contrast, steps such as PCR and nucleotide detection have customarily only been within the compass of specially trained individuals having access to specialist equipment.

Sample preparation is labor intensive in part because most samples must be heated at one or more stages, and in part because target polynucleotides are typically captured by some kind of retention member which must then be effectively isolated from the surrounding milieu. Thus, even where various liquid transfer operations can be optimized, and even automated, there is still a need for controlled application of heat, and efficient capture of extracted polynucleotides in situ.

The discussion of the background herein is included to explain the context of the inventions described herein. This is not to be taken as an admission that any of the material referred to was published, known, or part of the common general knowledge as at the priority date of any of the claims.

Throughout the description and claims of the specification the word "comprise" and variations thereof, such as "comprising" and "comprises", is not intended to exclude other additives, components, integers or steps.

SUMMARY

An apparatus for separating magnetic particles, comprising: one or more magnets affixed to a supporting member, a motorized mechanism configured to move the supporting member in such a manner that the one or more magnets move backwards and forwards along a fixed axis, and during at least a portion of the motion, the one or more magnets maintain close proximity to one or more receptacles which contain the magnetic particles; and control circuitry to control the motorized mechanism.

An integrated separator and heater, comprising: a heater assembly, wherein the heater assembly comprises a plurality of independently controllable heater units, each of which is configured to accept and to heat one of a plurality of process tubes; one or more magnets affixed to a supporting member, a motorized mechanism configured to move the supporting member in such a manner that the one or more magnets move backwards and forwards along a fixed axis, and during at least a portion of the motion the one or more magnets maintain close proximity to one or more of the process tubes in the heater assembly, wherein the one or more process tubes contain magnetic particles; and control circuitry to control the motorized mechanism and to control heating of the heater units.

A diagnostic apparatus comprising the integrated separator and heater as described herein.

A method of controllably heating a plurality of process tubes, each containing a solution of reagents and biological samples, wherein conditions in each of the process tubes may be individually tailored.

BRIEF DESCRIPTION OF THE DRAWINGS

Like reference numerals in the various drawings indicate like elements.

DETAILED DESCRIPTION

The heater and separator described herein are typically configured for use in a method and apparatus for carrying out sample preparation on biological samples in parallel, with or without PCR and detection on the prepared samples, and preferably with high throughput.

Apparatus Overview

Figure 1:
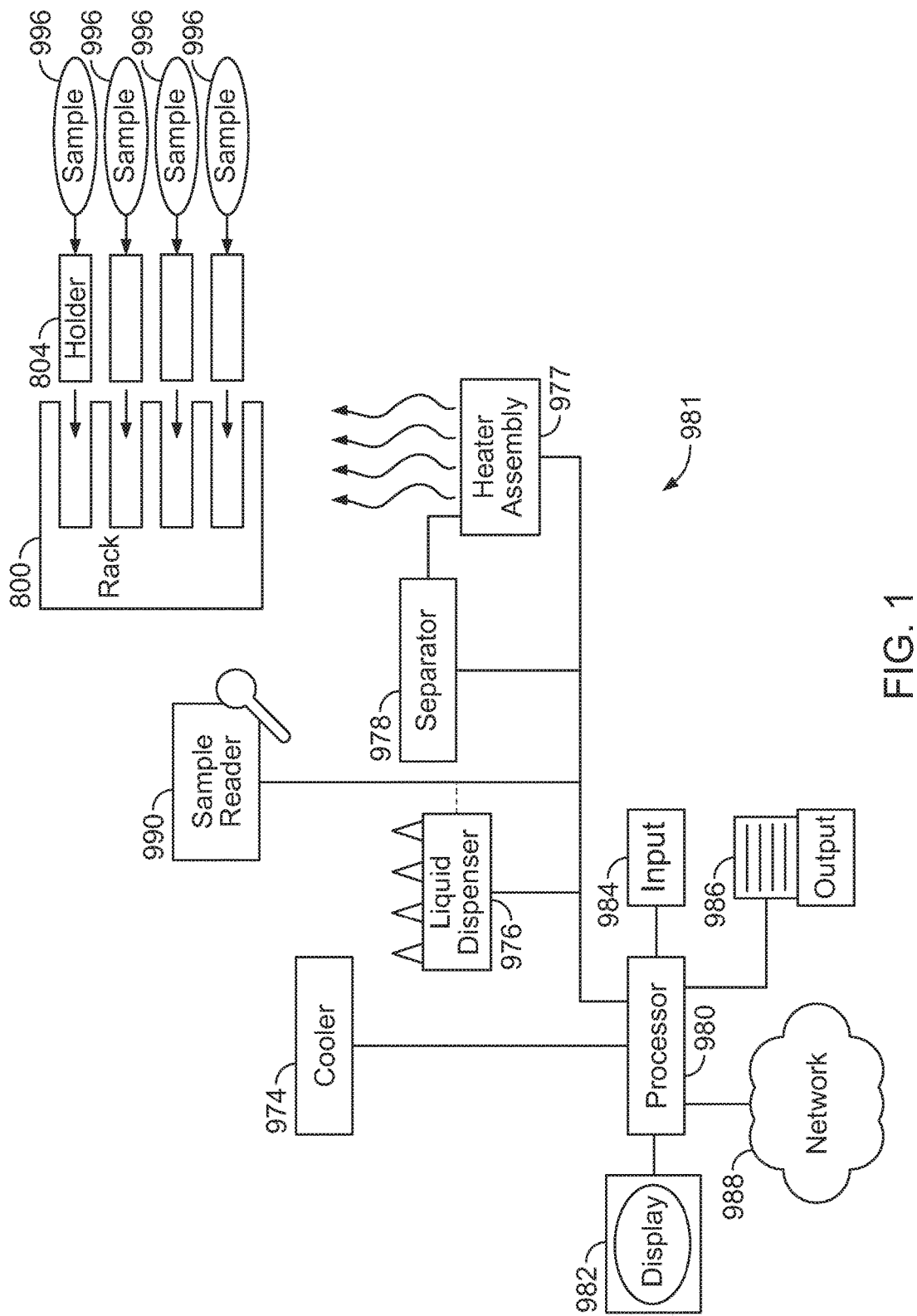
FIG. 1 shows a schematic of an automated apparatus configured to carry out sample preparation using a heater and separator as described herein.

A schematic overview of an apparatus 981 for carrying out automated sample preparation on multiple samples in parallel, according to steps exemplified elsewhere herein, is shown in FIG. 1. The geometric arrangement of the components of system 981 is exemplary and not intended to be limiting. The apparatus may additionally comprise (not shown in FIG. 1) a microfluidic cartridge, in a receiving bay, and configured to carry out a diagnostic test on the sample, such as by detecting presence of an amplified polynucleotide in the cartridge. Such additional features are also described in U.S. patent application Ser. No. 12/173,023, filed on Jul. 14, 2008 (and entitled "Integrated Apparatus for Performing Nucleic Acid Extraction and Diagnostic Testing on Multiple Biological Samples", in the name of Williams, et al.).

A processor 980, such as a microprocessor, is configured to control functions of various components of the system as shown, and is thereby in communication with each such component requiring control. It is to be understood that many such control functions can optionally be carried out manually, and not under control of the processor. Furthermore, the order in which the various functions are described, in the following, is not limiting upon the order in which the processor executes instructions when the apparatus is operating. Thus, processor 980 can be configured to receive data about a sample to be analyzed, e.g., from a sample reader 990, which may be a barcode reader, an optical character reader, or an RFID scanner (radio frequency tag reader).

Processor 980 can be configured to accept user instructions from an input device 984, where such instructions may include instructions to start analyzing the sample, and choices of operating conditions. Processor 980 can be also configured to communicate with a display 982, so that, for example, information about an analysis is transmitted to the display and thereby communicated to a user of the system. Such information includes but is not limited to: the current status of the apparatus; progress of PCR thermocycling; and a warning message in case of malfunction of either system or cartridge. Additionally, processor 980 may transmit one or more questions to be displayed on display 982 that prompt a user to provide input in response thereto. Thus, in certain embodiments, input 984 and display 982 are integrated with one another. Processor 980 can be optionally further configured to transmit results of an analysis to an output device 986 such as a printer, a visual display, a display that utilizes a holographic projection, or a speaker, or a combination thereof. Processor 980 can be still further optionally connected via a communication interface such as a network interface to a computer network 988.

Processor 980 can be further configured to control various aspects of sample preparation and diagnosis, as follows in overview. In FIG. 1, the apparatus 981 is configured to operate in conjunction with a complementary rack 800. Apparatus 981 may be capable of receiving multiple racks, such as 1, 2, 3, 4, or 6 racks.

Embodiments of rack 800 are further described in U.S. patent application Ser. No. 12/173,023, filed by ExpressMail on Jul. 14, 2008 (and entitled "Integrated Apparatus for Performing Nucleic Acid Extraction and Diagnostic Testing on Multiple Biological Samples", in the name of Williams, et al.), and Ser. No. 12/178,584, filed on even date herewith, and entitled "Rack For Sample Tubes And Reagent Holders", in the name of Duffy, et al., both of which are incorporated herein by reference in their entireties. A rack 800 is itself configured to receive a number of biological samples 996 in a form suitable for work-up and diagnostic analysis, and a number of holders 804—as further described herein, such as in connection with FIGS. 2A and 2B, that are equipped with various reagents, pipette tips and receptacles. The rack is configured so that, during sample work-up, samples are processed in the respective holders, the processing including being subjected, individually, to heating and cooling via heater assembly 977.

The heating functions of the heater assembly 977 can be controlled by the processor 980. Heater assembly 977 operates in conjunction with a separator 978, such as a magnetic separator, that also can be controlled by processor 980 to move into and out of close proximity to one or more processing chambers associated with the holders 804, wherein particles such as magnetic particles are present. Assembly 977 and separator 978 are further described herein.

Liquid dispenser 976, which similarly can be controlled by processor 980, is configured to carry out various suck and dispense operations on respective sample, fluids and reagents in the holders 804, to achieve extraction of nucleic acid from the samples. Liquid dispenser 976 can carry out such operations on multiple holders simultaneously.

Sample reader 990 is configured to transmit identifying indicia about the sample, and in some instances the holder, to processor 980. In some embodiments a sample reader is attached to the liquid dispenser and can thereby read indicia about a sample above which the liquid dispenser is situated. In other embodiments the sample reader is not attached to the liquid dispenser and is independently movable, under control of the processor. Liquid dispenser 976 is also configured to take aliquots of fluid containing nucleic acid extracted from one or more samples and direct them to storage area 974, which may be a cooler. Area 974 contains, for example, a PCR tube corresponding to each sample.

Embodiments of the apparatus shown in outline in FIG. 1, as with other exemplary embodiments described herein, are advantageous because they do not require locations within the apparatus suitably configured for storage of reagents. Therefore, the apparatus in FIG. 1 is self-contained and operates in conjunction with holders 804, wherein the holders are pre-packaged with reagents, such as in locations within it dedicated to reagent storage.

The apparatus of FIG. 1 may be configured to carry out operation in a single location, such as a laboratory setting, or may be portable so that they can accompany, e.g., a physician, or other healthcare professional, who may visit patients at different locations. The apparatus is typically provided with a power-cord so that they can accept AC power from a mains supply or generator. The apparatus may also be configured to operate by using one or more batteries and therefore is also typically equipped with a battery recharging system, and various warning devices that alert a user if battery power is becoming too low to reliably initiate or complete a diagnostic analysis.

The apparatus of FIG. 1 may further be configured, in other embodiments, for multiplexed sample analysis and/or analysis of multiple batches of samples, where, e.g., a single rack holds a single batch of samples. Each component shown in FIG. 1 may therefore be present as many times as there are batches of samples, though the various components may be configured in a common housing.

The apparatuses as described herein find application to analyzing any nucleic acid containing sample for any purpose, including but not limited to genetic testing, and clinical testing for various infectious diseases in humans.

The apparatus herein can be configured to run on a laboratory benchtop, or similar environment, and can test approximately 45 samples per hour when run continuously throughout a normal working day. Results from individual raw samples are typically available in less than 1 hour.

Heater Assembly

Figure 3:
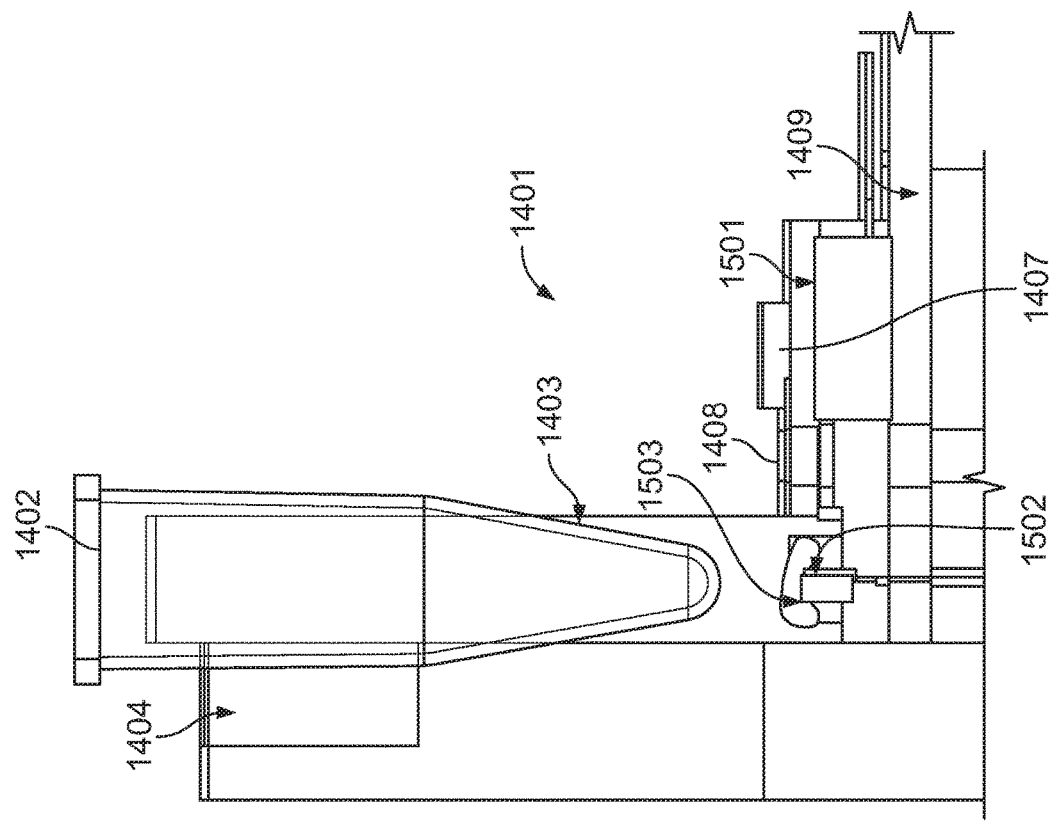
FIG. 3 shows a heater unit in perspective and cross-sectional view.
Figure 3:
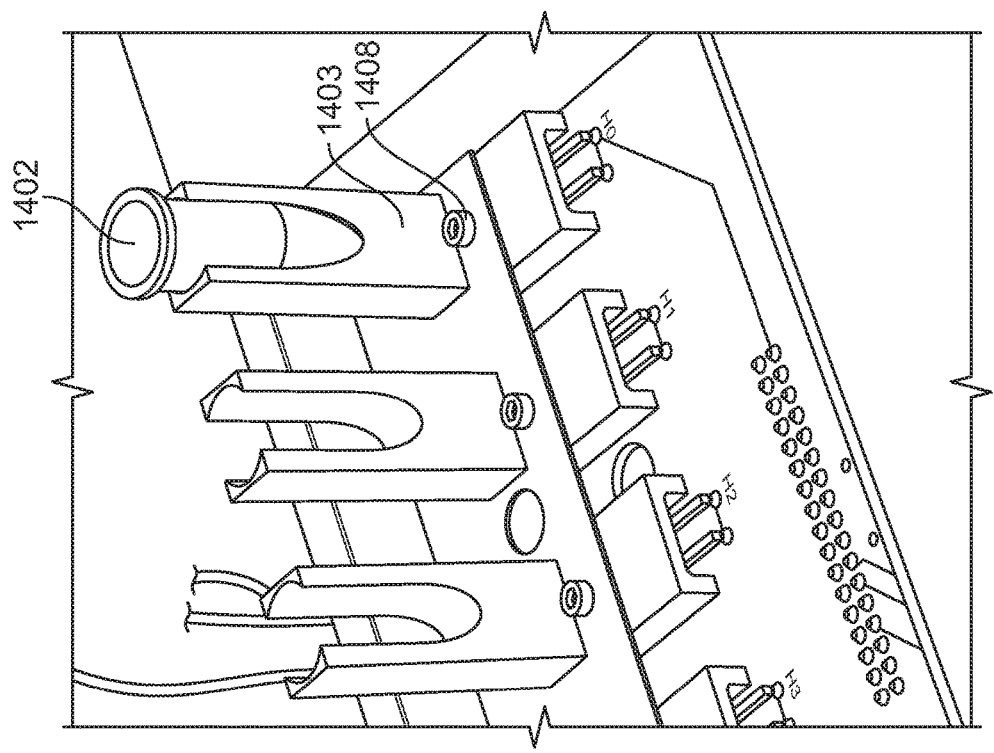

A cross-sectional view of a heater unit of an exemplary heater assembly 1401 is shown in FIG. 3 (right hand panel). The heater assembly comprises one or more independently controllable heater units, each of which comprises a heat block. In certain embodiments there are 2, 3, 4, 5, 6, 8, 10, 12, 16, 20, 24, 25, 30, 32, 36, 40, 48, or 50 heater units in a heater assembly. Still other numbers of heater units, such as any number between 6 and 100 are consistent with the description herein. The one or more heat blocks may be fashioned from a single piece of metal or other material, or may be made separately from one another and mounted independently of one another or connected to one another in some way. Thus, the term heater assembly connotes a collection of heater units but does not require the heater units or their respective heat blocks to be attached directly or indirectly to one another. The heater assembly can be configured so that each heater unit independently heats each of the one or more process tubes 1402, for example by permitting each of the one or more heat blocks to be independently controllable, as further described herein.

In the configuration of FIG. 3, the heater assembly comprises one or more heat blocks 1403 each of which is configured to align with and to deliver heat to a process tube 1402. Each heat block 1403 can be optionally secured and connected to the rest of the apparatus using a strip 1408 and one or more screws 1407 or other adhesive device(s). This securing mechanism is not limited to such a configuration.

Although a cross-sectional view of one heat block 1403 is shown in FIG. 3, it should be understood that this is consistent with having multiple heat blocks aligned in parallel to one another and such that their geometric midpoints all lie on a single linear axis, though it is not so limited in configuration. Thus, the one or more heat blocks may be positioned at different heights from one another, in groups or, alternately, individually, or may be staggered with respect to one another from left to right in FIG. 3 (right hand panel), in groups or alternately, or individually. Additionally, and in other embodiments, the heat blocks are not aligned parallel to one another but are disposed at angles relative to one another, the angles being other than 180°. Furthermore, although the heat block shown in FIG. 3 may be one of several that are identical in size, it is consistent with the technology herein that one or more heat blocks may be configured to accept and to heat process tubes of different sizes.

The exemplary heat block 1403 in FIG. 3 (right hand panel) is configured to have an internal cavity that partially surrounds a lower portion of process tube 1402. In the heat block of FIG. 3, the internal cavity surrounds the lower portion of process tube 1402 on two sides but not the front side (facing away from magnet 1404) and not the rear side (adjacent to magnet 1404). In other embodiments, heat block 1403 is configured to surround the bottom of process tube 1402 on three sides, including the front side. Still other configurations of heat block 1403 are possible, consistent with the goals of achieving rapid and uniform heating of the contents of process tube 1402. In certain embodiments, the heat block is shaped to conform closely to the shape of process tube 1402 so as to increase the surface area of the heat block that is in contact with the process tube during heating of the process tube. Thus, although exemplary heat block 1403 is shown having a conical, curve-bottomed cavity in which a complementary process tube is seated, other embodiments of heat block 1403 have, for example, a cylindrical cavity with a flat bottom. Still other embodiments of heat block 1403 may have a rectilinear internal cavity such as would accommodate a cuvette.

Moreover, although heat block 1403 is shown as an L-shape in FIG. 3, which aids in the transmittal of heat from heating element 1501 and in securing the one or more heat blocks to the rest of the apparatus, it need not be so, as further described herein. For example, in some embodiments heating element 1501 may be positioned directly underneath process tube 1402.

Each heat block 1403 is configured to have a low thermal mass while still maintaining high structural integrity and allowing a magnet to slide past the heat blocks and the process tubes with ease. A low thermal mass is advantageous because it allows heat to be delivered or dissipated rapidly, thus increasing the heating and cooling efficiency of the apparatus in which the heater assembly is situated. Factors that contribute to a low thermal mass include the material from which a heat block is made, and the shape that it adopts. The heat blocks 1403 can therefore be made of such materials as aluminum, silver, gold, and copper, and alloys thereof, but are not so limited.

In one embodiment, the heat block 1403 has a mass of ~10 grams and is configured to heat up liquid samples having volumes between 1.2 ml and 10 µl. Heating from room temperature to 65° C. for a 1 ml biological sample can be achieved in less than 3 minutes, and 10 µl of an aqueous liquid such as a release buffer up to 85° C. (from 50° C.) in less than 2 minutes. The heat block 1403 can cool down to 50° C. from 85° C. in less than 3 minutes. The heat block 1403 can be configured to have a temperature uniformity of 65±4° C. for heating up 1 ml of sample and 85±3° C. for heating up 10 µl of release buffer. These ranges are typical, but the heat block can be suitably scaled to heat other volumes of liquid at rates that are slower and faster than those described. This aspect of the technology is one aspect that contributes to achieving rapid nucleic acid extraction of multiple samples by combination of liquid processing steps, rapid heating for lysis, DNA capture and release and magnetic separation, as further described herein and elsewhere, such as U.S. patent application Ser. Nos. 12/172,208 and 12/172,214, both of which are incorporated herein by reference.

Not shown in FIG. 3, the heater assembly 1401 can also optionally be contained in an enclosure that surrounds the heat blocks 1403. The enclosure can be configured to enable sufficient air flow around the process tubes and so as not to significantly inhibit rate of cooling. The enclosure can have a gap between it and the heat blocks to facilitate cooling. The enclosure can be made of plastic, but is not so limited. The enclosure is typically configured to appear aesthetic to a user.

As shown in FIG. 3, the heater assembly 1401 can also comprise one or more heating elements (e.g., a power resistor) 1501 each of which is configured to thermally interface to a heat block 1403 and dissipate heat to it. For example, in one embodiment, a power resistor can dissipate up to 25 Watts of power. A power resistor is advantageous because it is typically a low-cost alternative to a heating element. Other off-the-shelf electronic components such as power transistors may also be used to both sense temperature and heat. Although the heating element 1501 is shown placed at the bottom of the heat block 1403, it would be understood that other configurations are consistent with the assembly described herein: for example, the heating element 1501 might be placed at the top or side of each heat block 1403, or directly underneath process tube 1402. In other embodiments, the heating element has other shapes and is not rectangular in cross section but may be curved, such as spherical or ellipsoidal. Additionally, the heating element may be moulded or shaped so that it conforms closely or approximately to the shape of the bottom of the process tube. Not shown in FIG. 3, the heater assembly can also comprise an interface material (e.g., Berquist q-pad, or thermal grease) between the heating element 1501 and the heat block 1403 to enable good thermal contact between the element and the heat block.

In the embodiment shown in FIG. 3, the heater assembly further comprises one or more temperature sensors 1502, such as resistive temperature detectors, to sense the respective temperatures of each heat block 1403. Although a temperature sensor 1502 is shown placed at the bottom of the heat block 1403, it would be understood that other configurations are consistent with the assembly described herein: for example, the temperature sensor might be placed at the top or side of each heat block 1403, or closer to the bottom of process tube 1402 but not so close as to impede uniform heating thereof. As shown in the embodiment of FIG. 3, the heater assembly can further comprise an interface material (e.g., Berquist q-pad) 1503 configured to enable good thermal contact between the sensor 1502 and the heat block 1403, to thereby ensure an accurate reading.

Certain embodiments of the diagnostic or preparatory apparatus herein have more than one heater assembly as further described herein. For example, a single heater assembly may be configured to independently heat 6 or 12 process tubes, and an apparatus may be configured with two or four such heater assemblies.

Rack

Figure 4:
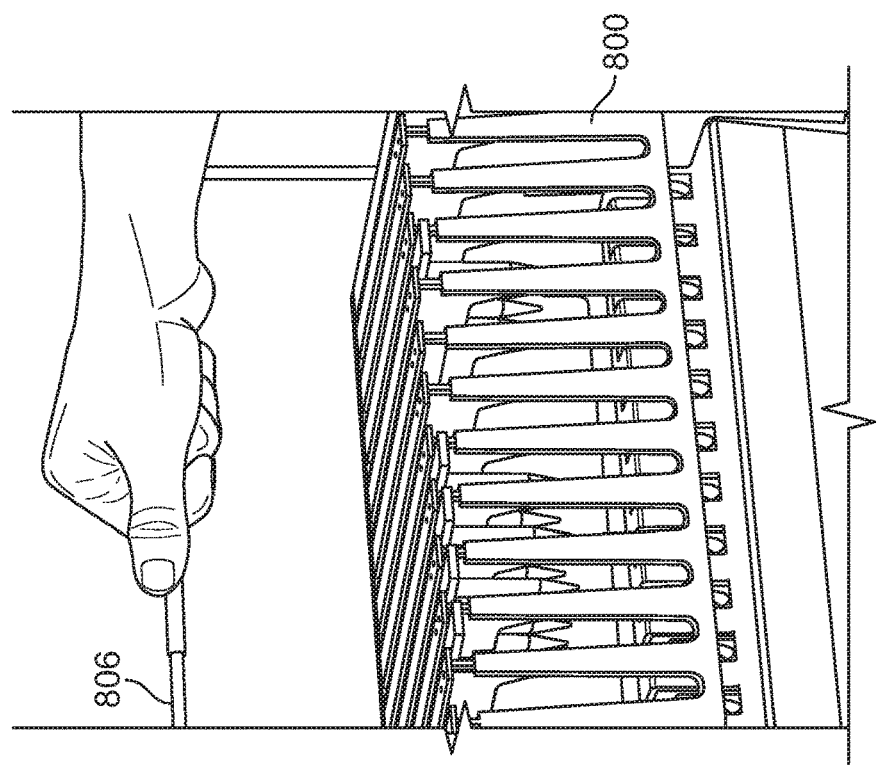
FIG. 4 shows perspective views of the rack of reagent holders and sample tubes of FIG. 5, in conjunction with a heater unit.
Figure 4:
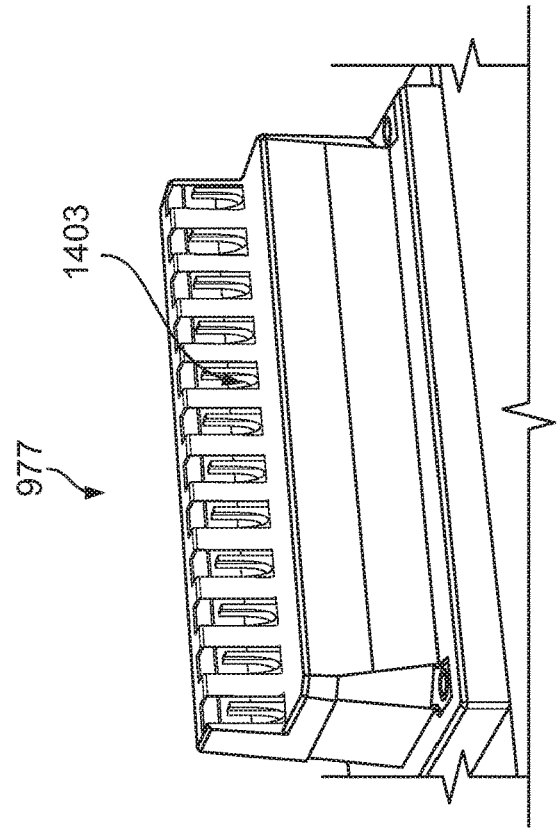

Process tubes 1402 are typically disposed in reagent holders that themselves are supported in a rack, as shown in FIG. 4, the combination of reagent holders and rack ensuring that the process tubes are effectively located in proximity to the heater units.

The racks for use herein are typically configured to be insertable into, and removable from, a diagnostic or preparatory apparatus as further described herein, each of the racks being further configured to receive a plurality of reagent holders, and to receive a plurality of sample tubes, wherein the reagent holders are in one-to-one correspondence with the sample tubes, and wherein the reagent holders each contain sufficient reagents to extract polynucleotides from a sample and place the polynucleotides into a PCR-ready form. Exemplary reagent holders are further described elsewhere herein and also in copending application Ser. No. 12/218,416, filed by ExpressMail on Jul. 14, 2008 (and entitled "Reagent Tube, Reagent Holder, and Kits Containing Same", in the name of Wilson, et al.) and incorporated herein by reference. An exemplary apparatus is outlined herein, and also described in U.S. patent application Ser. No. 12/173,023, filed by ExpressMail on Jul. 14, 2008 (and entitled "Integrated Apparatus for Performing Nucleic Acid Extraction and Diagnostic Testing on Multiple Biological Samples", in the name of Williams, et al.), incorporated by reference herein.

Figure 5:
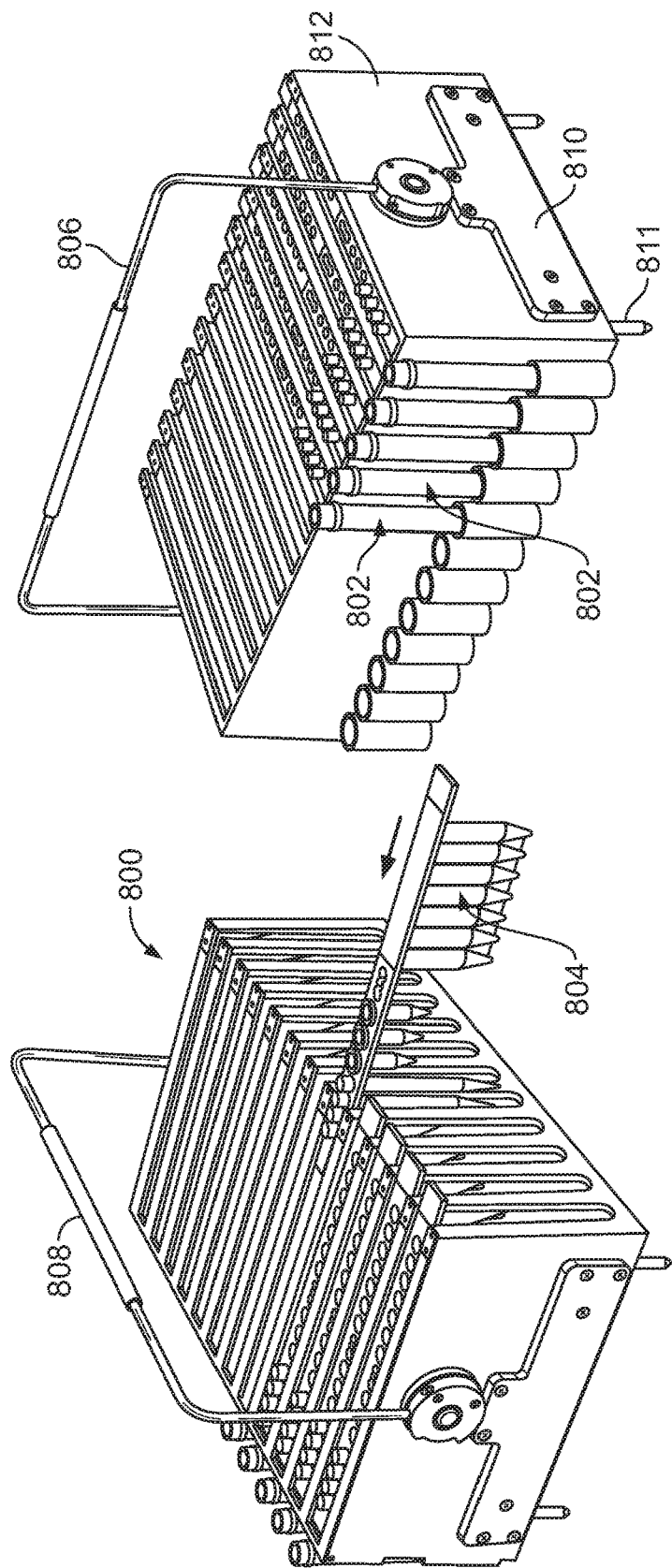
FIG. 5 shows perspective views of an exemplary rack for samples and reagent holders.

Two perspective views of an exemplary rack 800, configured to accept 12 sample tubes and 12 corresponding reagent holders, in 12 lanes, are shown in FIG. 5. A lane, as used herein in the context of a rack, is a dedicated region of the rack designed to receive a sample tube and corresponding reagent holder. A perspective view of the same exemplary rack, in conjunction with a heater unit, as further described herein, is shown in FIG. 4.

A rack may accept 2, 4, 6, 8, 10, 12, 16, or 20 samples such as in sample tubes 802, and a corresponding number of holders 804. Thus the embodiment of FIG. 5 configured to receive 12 samples and 12 corresponding reagent holders is exemplary.

Magnetic Separator

The disclosure herein further comprises a magnetic separator, configured to separate magnetic particles, the separator comprising: one or more magnets affixed to a supporting member; a motorized mechanism configured to move the supporting member in such a manner that the one or more magnets move backwards and forwards along a fixed axis, and during at least a portion of the motion, the one or more magnets maintain close proximity to one or more receptacles which contain the magnetic particles in solution; and control circuitry to control the motorized mechanism.

The disclosure herein still further includes an integrated magnetic separator and heater, comprising: a heater assembly, wherein the heater assembly comprises a plurality of independently controllable heater units, each of which is configured to accept and to heat one of a plurality of process tubes; one or more magnets affixed to a supporting member, a motorized mechanism configured to move the supporting member in such a manner that the one or more magnets move backwards and forwards along a fixed axis, and during at least a portion of the motion the one or more magnets maintain close proximity to one or more of the process tubes in the heater assembly, wherein the one or more process tubes contain magnetic particles; and control circuitry to control the motorized mechanism and to control heating of the heater units.

Typically, each of the one or more receptacles is a process tube, such as for carrying out biological reactions. In some embodiments, close proximity can be defined as a magnet having a face less than 2 mm away from the exterior surface of a process tube without being in contact with the tube. It can still further be defined to be less than 1 mm away without being in contact with the tube, or between 1 and 2 mm away.

Typically the magnetic particles are microparticles, beads, or microspheres capable of binding one or more biomolecules, such as polynucleotides, and commonly available as retention members. Separating the particles, while in solution, typically comprises collecting and concentrating, or gathering, the particles into one location in the inside of the one or more receptacles.

Figure 6:
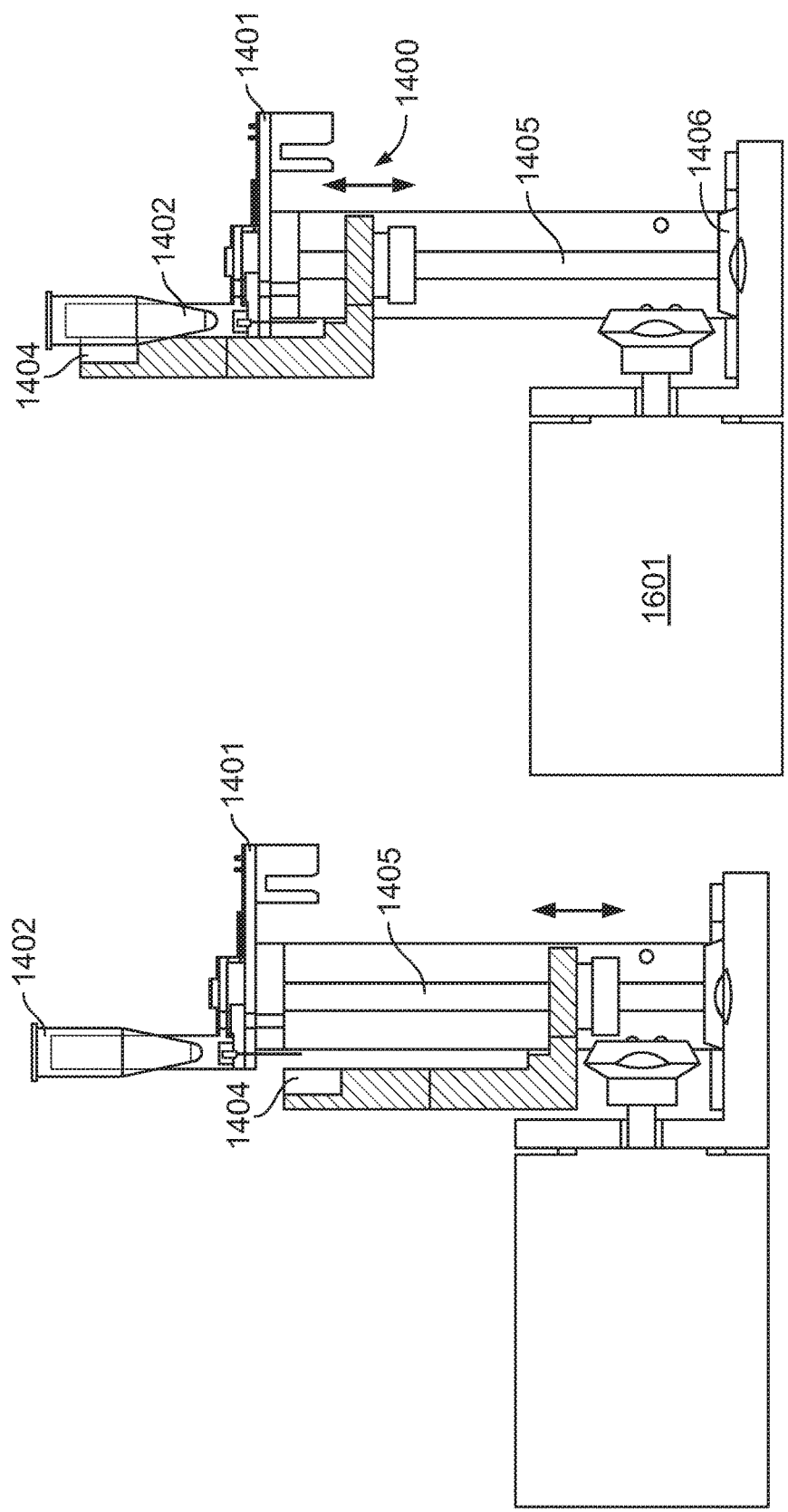
FIG. 6 shows an integrated heater and separator unit in cross-sectional view.

An exemplary magnetic separator 1400 is shown in FIG. 6, configured to operate in conjunction with heater assembly 1401. The magnetic separator 1400 is configured to move one or more magnets relative to the one or more process tubes 1402. While the magnet 1404 shown in FIG. 6 is shown as a rectangular block, it is not so limited in shape. Moreover, the configuration of FIG. 6 is consistent with either having a single magnet that extends across all heat blocks 1403 or having multiple magnets operating in concert and aligned to span a subset of the heat blocks, for example, aligned collinearly on the supporting member. The magnet 1404 can be made of neodymium (e.g., from K & J Magnetics, Inc.) and can have a magnetic strength of 5,000-15,000 Gauss (Brmax). The poles of the magnets 1404 can be arranged such that one pole faces the heat blocks 1403 and the other faces away from the heat blocks.

Further, in the embodiment shown in FIG. 6, the magnet 1404 is mounted on a supporting member 1505 that can be raised up and down along a fixed axis using a motorized shaft 1405. The fixed axis can be vertical. In the embodiment shown in FIG. 6, a geared arrangement 1406 enables the motor 1601 to be placed perpendicular to the shaft 1405, thereby saving space in the apparatus in which magnetic separator 1400 is situated. In other embodiments, the motor is placed underneath shaft 1405. It would be understood that other configurations are consistent with the movement of the magnet relative to the process tubes, including, but not limited to, moving the magnet from side-to-side, or bringing the magnet down from above. The motor can be computer controlled to run at a particular speed; for example at a rotational speed that leads to vertical motion of the magnet in the range 1-20 mm/s. The magnetic separator can thus be configured to move repetitively, e.g., up an down, from side to side, or backwards and forwards, along the same axis several times. In some embodiments there is more than one shaft that operates under motorized control. The presence of at least a second shaft has the effect of making the motion of the separator more smooth. In some embodiments, the supporting member rides on one more guiding members to ensure that the supporting member does not, for example, tip, twist, or yaw, or undergo other internal motions while moving (other than that of controlled motion along the axis) and thereby reduce efficacy of the separation.

The supporting member can also be configured to move the magnets between a first position, situated away from the one or more receptacles, and a second position situated in close proximity to the one or more receptacles, and is further configured to move at an amplitude about the second position where the amplitude is smaller than a distance between the first position and the second position as measured along the shaft.

Shown in FIGS. 3 and 6, the heater assembly 1401 and the magnetic separator 1400 can be controlled by electronic circuitry such as on printed circuit board 1409. The electronic circuitry 1409 can be configured to cause the heater assembly 1401 to apply heat independently to the process tubes 1402 to minimize the cost of heating and sensing. It can also be configured to cause the magnetic separator 1400 to move repetitively relative to the process tubes 1402. The electronic circuitry 1409 can be integrated into a single printed circuit board (PCB). During assembly, a plastic guide piece can help maintain certain spacing between individual heat blocks 1403. This design can benefit from use of off-the-shelf electronics to control a custom arrangement of heat blocks 1403.

Not shown in FIGS. 3 and 6, an enclosure can cover the magnetic separator 1400 and the heater assembly 1401 for protection of sub-assemblies below and aesthetics. The enclosure can also be designed to keep the heat blocks 1403 spaced apart from one another to ensure efficiency of heating and cooling. The magnetic separator and heater assembly can, alternatively, be enclosed by separate enclosures. The one or more enclosures can be made of plastic.

Advantageously, the heater assembly and magnetic separator operate together to permit successive heating and separation operations to be performed on liquid materials in the one or more process tubes without transporting either the liquid materials or the process tubes to different locations to perform either heating or separation. Such operation is also advantageous because it means that the functions of heating and separation which, although independent of one another, are both utilized in sample preparation, may be performed with a compact and efficient apparatus.

Reagent Holders

Described herein and elsewhere are reagent holders for holding and transporting reagents for various purposes, in particular sample preparation in a clinical context, and configured to be received by a rack as described herein. The reagent holders also typically provide a container in which various reagents can be mixed one with another and/or with a sample. The holders are also configured for use in an automated preparatory apparatus that can carry out sample preparation on samples in more than one holder simultaneously.

Figure 2A:
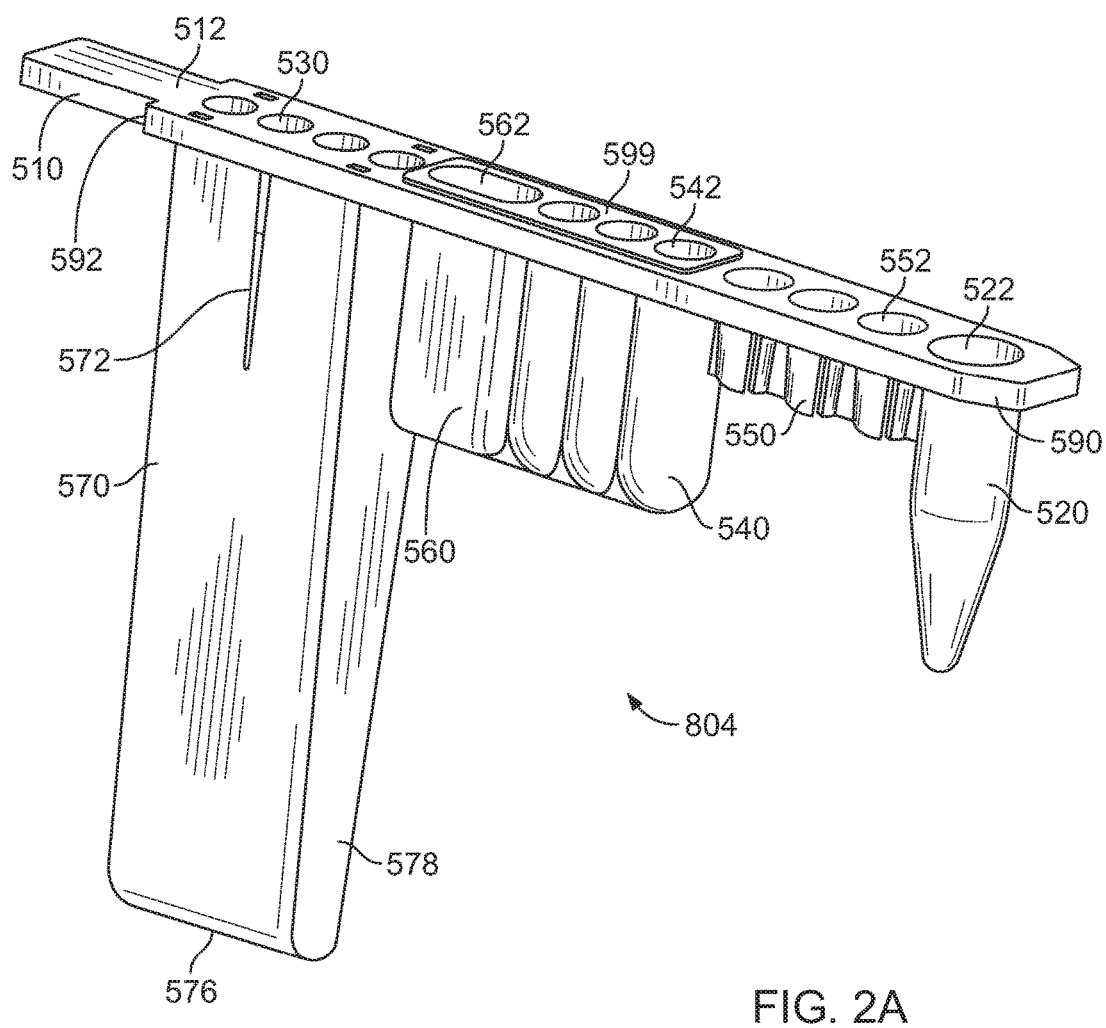
FIGS. 2A and 2B show an exemplary embodiment of a reagent holder, in perspective view (FIG. 2A), and underside view (FIG. 2B).
Figure 2B:
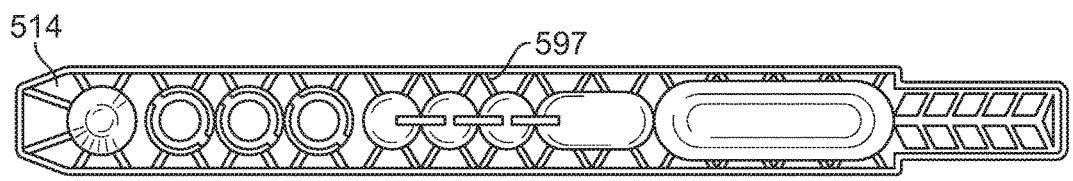

FIGS. 2A and 2B show views of an exemplary holder 804 as further described herein. This exemplary holder, as well as others consistent with the written description herein though not shown as specific embodiments, are now described. Further details of reagent holders can be found in U.S. patent application Ser. No. 12/218,416, filed by Express Mail Jul. 14, 2008 in the name of Wilson, et al., and entitled "Reagent Tube, Reagent Holder, and Kits Containing Same", which is incorporated herein by reference.

The exemplary holder of FIG. 2A comprises a connecting member 510 having one or more characteristics as follows. Connecting member 510 serves to connect various components of the holder together. Connecting member 510 has an upper side 512 and, opposed to the upper side, an underside 514.

The reagent holder of FIG. 2A is configured to comprise: a process tube 520 affixed to the connecting member and having an aperture 522 located in the connecting member, at least one socket 530, located in the connecting member, the socket configured to accept a disposable pipette tip 580; an optional pipette sheath 570 as further described herein; two or more reagent tubes 540 disposed on the underside of the connecting member, each of the reagent tubes having an inlet aperture 542 located in the connecting member, and one or more receptacles 550, located in the connecting member, wherein the one or more receptacles are each configured to receive a complementary container such as a reagent tube (not shown) inserted from the upper side 512 of the connecting member. The lanes of the rack described herein are designed to have sufficient depth and width to accommodate the various reagent tubes, receptacles, process tube, and pipette sheath of a given reagent holder, and to position the process tube in communication with a heater/separator unit.

In FIG. 2B, a view of underside 514 is shown, having various struts 597 connecting a rim of the connecting member with variously the sockets, process tube, and reagent tubes. Struts 597 are optional, and may be omitted all or in part, or may be substituted by, in all or in part, other supporting pieces that connect various parts of the holder to one another.

The one or more receptacles 550 are configured to accept reagent tubes that contain, respectively, sufficient quantities of one or more reagents typically in solid form, such as in lyophilized form, for carrying out extraction of nucleic acids from a sample that is associated with the holder. The receptacles can be all of the same size and shape, or may be of different sizes and shapes from one another. Receptacles 550 are shown as having open bottoms, but are not limited to such topologies, and may be closed other than the inlet 552 in the upper side of connecting member 510. Preferably the receptacles 550 are configured to accept commonly used containers in the field of laboratory analysis, or containers suitably configured for use with the holder herein.

In one embodiment, the containers 554 containing lyophilized reagents, disposed in the receptacles 550, are 0.3 ml tubes that have been further configured to have a star-shaped pattern on their respective bottom interior surfaces. This is so that when a fluid has been added to the lyophilized reagents (which are dry in the initial package), a pipette tip can be bottomed out in the tube and still be able to withdraw almost the entire fluid from the tube. The design of the star-pattern is further described elsewhere in U.S. patent application Ser. No. 12/178,557, filed on even date herewith, and entitled "Reagent Tube", in the name of Handique et al., which application is incorporated herein by reference.

The embodiment of a reagent holder 804 is shown configured with a waste chamber 560, having an inlet aperture 562 in the upper side of the connecting member. Waste chamber 560 is optional and, in embodiments where it is present, is configured to receive spent liquid reagents. In other embodiments, where it is not present, spent liquid reagents can be transferred to and disposed of at a location outside of the holder, such as, for example, a sample tube that contained the original sample whose contents are being analyzed.

The embodiment of a reagent holder 804 is shown having a pipette sheath 570. This is an optional component of the holders described herein. It may be permanently or removably affixed to connecting member 510, or may be formed, e.g., moulded, as a part of a single piece assembly for the holder. Pipette sheath 570 is typically configured to surround the at least one socket and a tip and lower portion of a pipette tip when the pipette tip is stationed in the at least one socket. In some embodiments, the at least one socket comprises four sockets. In some embodiments the at least one socket comprises two, three, five, or six sockets.

Pipette sheath 570 typically is configured to have a bottom 576 and a walled portion 578 disposed between the bottom and the connecting member. Pipette sheath 570 may additionally and optionally have one or more cut-out portions 572 in the wall 578, or in the bottom 576. In embodiments of the reagent holder having a pipette sheath, a purpose of the sheath is to catch drips from used pipette tips, and thereby to prevent cross-sample contamination, from use of one holder to another in a similar location, and/or to any supporting rack in which the holder is situated. Typically, then, the bottom 576 is solid and bowl-shaped (concave) so that drips are retained within it. An embodiment having no pipette sheath, could utilize, e.g., a drip tray or a drainage outlet, suitably placed beneath pipette tips located in the one or more sockets, for the same purpose and located under or in the bottom of the rack, as described herein.

Process tube 520 can also be a snap-in tube, rather than being part of an integrated piece. Process tube 520 is typically used for various mixing and reacting processes that occur during sample preparation. For example, cell lysis can occur in process tube 520, as can extraction of nucleic acids, such as DNA or RNA of a patient, and DNA or RNA of a pathogen. Process tube 520 is then advantageously positioned in a location that minimizes, overall, pipette head moving operations involved with transferring liquids to process tube 520. Process tube 520 is also located in the holder in such a position that, when the holder is inserted in a rack as further described herein, the process tube is exposed and accessible to a heater and separator, as further described herein.

Some of the reagents contained in the holder are provided as liquids, and others may be provided as solids. In some embodiments, a different type of container or tube is used to store liquids from those that store the solids.

Reagent tubes 540 are typically configured to hold liquid reagents, one per tube. For example, in reagent holder embodiment 804, three reagent tubes are shown, containing respectively wash buffer, release buffer, and neutralization buffer, each of which is used in a sample preparation protocol.

The reagent holder embodiment 804 has a connecting member that is configured so that the at least one socket, the one or more receptacles, and the respective apertures of the process tube, and the two or more reagent tubes, are all arranged linearly with respect to one another (i.e., their midpoints lie on the same axis). However, the holders herein are not limited to particular configurations of receptacles, process tube, sockets, reagent tubes, and waste chamber if present. For example, a holder may be made shorter, if some apertures are staggered with respect to one another and occupy 'off-axis' positions. The various receptacles, etc., also do not need to occupy positions with respect to one another that are the same as those shown in FIGS. 2A and 2B. Thus, in FIGS. 2A and 2B, the process tube is on one end of the connecting member, and the pipette sheath is at the other end, adjacent to, in an interior position, a waste chamber and two or more reagent tubes. Still other dispositions are possible, such as mounting the process tube on one end of the holder, mounting the process tube adjacent the pipette tips and pipette tip sheath (as further described herein), and mounting the waste tube adjacent the process tube. It would be understood that alternative configurations of the various parts of the holder give rise only to variations of form and can be accommodated within other variations of the apparatus as described, including but not limited to alternative instruction sets for a liquid dispensing pipette head, heater assembly, and magnetic separator, as further described herein. Each such configuration of the reagent holder can be accommodated by a corresponding variation in form of the rack described herein that receives one or more such holders.

The process tube also may have a low binding surface, and allows magnetic beads to slide up and down the inside wall easily without sticking to it. Moreover, it has a hydrophobic surface coating enabling low stiction of fluid and hence low binding of nucleic acids and other molecules.

In some embodiments, the holder comprises a registration member such as a mechanical key. Typically such a key is part of the connecting member 510. A mechanical key ensures that the holder is accepted by a complementary member in, for example, a supporting rack as described herein or a receiving bay of an apparatus that controls pipetting operations on reagents in the holder. Thus, embodiment 804 has a mechanical key 592 that comprises a pair of rectangular-shaped cut-outs on one end of the connecting member. This feature as shown additionally provides for a tab by which a user may gain a suitable purchase when inserting and removing the holder into a rack or another apparatus. Embodiment 804 also has a mechanical key 590 at the other end of connecting member 510. Key 590 is an angled cutout that eases insertion of the holder into a rack, as well as ensures a good registration therein when abutting a complementary angled cut out in a recessed area configured to receive the holder.

A reagent holder for use with a rack as described herein is typically made of a plastic such as polypropylene. The plastic is such that it has some flexibility to facilitate placement into a rack, as further described herein. The plastic is typically sufficiently rigid, however, so that the holder will not significantly sag or flex under its own weight and will not easily deform during routine handling and transport, and thus will not permit reagents to leak out from it.

The holder is typically such that the connecting member, process tube, the two or more reagent tubes, and the waste chamber (if present) are made from a single piece, made from a material such as polypropylene.

Liquid Dispenser

Additionally, the heater and separator described herein can be configured to operate in conjunction with liquid processing operations, such as carried out by an automated pipette head. An exemplary automated pipette head is described in U.S. provisional application Ser. No. 60/959,437, filed Jul. 13, 2008, and in U.S. patent application Ser. No. 12/173,023, filed Jul. 14, 2008, entitled "Integrated Apparatus for Performing Nucleic Acid Extraction and Diagnostic Testing on Multiple Biological Samples", in the name of Williams, et al., all of which are incorporated herein by reference in their entirety. As reactions are carried out in a process tube that, for example, is part of a reagent holder as described elsewhere herein, the heater is controllably heated at various stages as desired and in concert with various pipetting operations. Similarly, the magnetic separator is controllably brought into proximity with a process tube as required at various stages in a process.

Typical features of an automated pipette head suitable for operating with the heater and separator as described herein include at least: an ability to pick up pipette tips from the one or more sockets in a reagent holder, and to return pipette tips to such sockets after use; to strip and discard a pipette tip from a pipette head after use or upon encountering an error, move a pipette tip with precision from one location of a given holder to another so that, for example, liquid reagents can be located and added to solid reagents to make up solutions, and various liquid reagents can be mixed with one another during a sample preparation protocol. Furthermore, it is desirable that such an automated pipette device can operate on several, such as 2, 3, 4, or 6, holders simultaneously when received by a rack, and thereby perform certain operations in parallel. Thus the pipette head should move in three degrees of freedom.

EXAMPLES

Example 1: Integrated Heater/Separator

Figure 7:
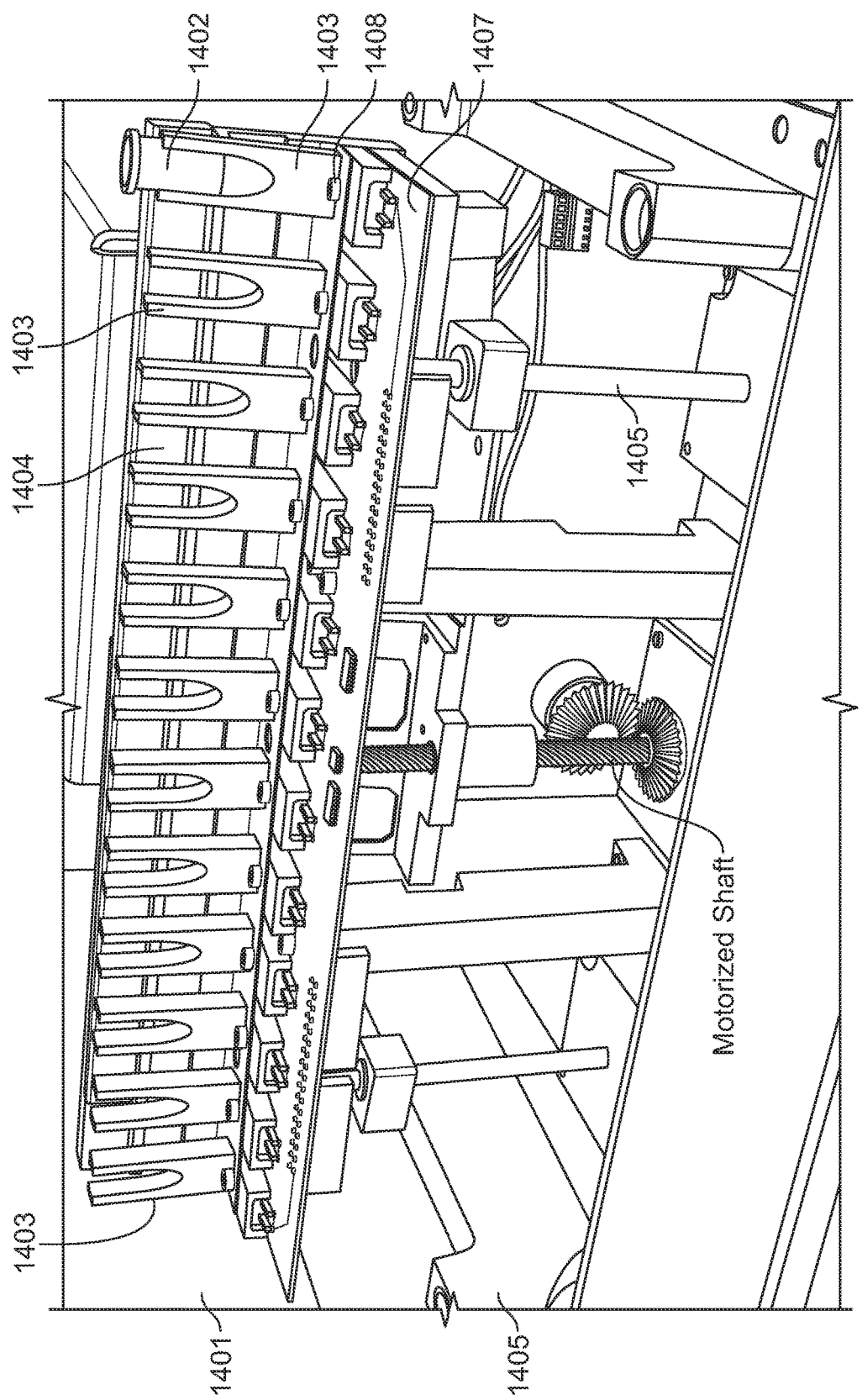
FIG. 7 shows an exemplary heater/separator.

In FIG. 7 an exemplary integrated magnetic separator and heater assembly are shown. Magnetic separator 1400 and heater assembly 1401 were fabricated comprising twelve heat blocks aligned parallel to one another. Each heat block 1403 is made from aluminum, and has an L-shaped configuration having a U-shaped inlet for accepting a process chamber 1402. Each heat block 1403 is secured and connected by a metal strip 1408 and screws 1407. Magnet 1404 is a rectangular block Neodymium (or other permanent rare earth materials, K & J Magnetics, Forcefield Magnetics) disposed behind each heat block 1403 and mounted on a supporting member. Gears 1406 communicate rotational energy from a motor (not shown) to cause the motorized shaft 1405 to raise and lower magnet 1404 relative to each heat block. The motor is computer-controlled to move the magnet at speeds of 1-20 mm/s. The device further comprises a printed circuit board (PCB) 1409 configured to cause the heater assembly to apply heat independently to each process chamber 1402 upon receipt of appropriate instructions. In the exemplary embodiment, the device also comprises a temperature sensor and a power resistor in conjunction with each heater block.

Example 2: Exemplary Chemistry Processes Performed by an Automated Instrument

Sample Pre-Processing

For Urine Sample: Take 0.5 ml of urine and mix it with 0.5 ml of collection buffer. Filter the sample through a pre-filter (containing two membranes of 10 micron and 3 micron pore size). Place the sample tube in the position specified for the external sample tube in a 12-holder rack.

For Plasma Sample: Take 0.5 ml of plasma and mix it with 0.5 ml of collection buffer. Place the sample tube in the position specified for the external sample tube in the 12-holder rack.

For GBS swab samples: Take the swab sample and dip it in 1 ml of collection buffer. Place the sample tube in the position specified for the external sample tube in the 12-holder rack.

The sample collection buffer contains 50 mM Tris pH 7, 1% Triton X-100, 20 mM Citrate, 20 mM Borate, 100 mM EDTA, plus 1,000 copies of positive control DNA.

Loading the Instrument and Starting Sample Processing

The following steps may be performed to initiate an analysis on samples in batch.
1. Load PCR tube containing PCR master mix in one of the specified snap-in location of the reagent holder.
2. Load PCR tube containing PCR probes and primers for the target analyte under consideration in the specified location of the reagent holder.
3. In case of two analyte test, load PCR tube containing probes and primers for second analyte in the specified location of the reagent holder.
4. Insert the reagent holder in a 12-holder rack in the same lane as the sample tube under consideration.
5. Prepare and insert reagent holders for other samples in consideration.
6. Load the 12-holder rack in one of the locations in the instrument.
7. Load a 12-sample cartridge in the cartridge tray loading position.
8. Start operation.

Liquid Processing Steps

The following steps may be performed to carry out sample preparation.
1. Using Pipette tip #1, the robot transfers the clinical sample from the external sample tube to the process tube of the reagent holder.
2. Using the same pipette tip, the robot takes about 100 μl of sample, mixes the lyophilized enzyme and affinity beads, transfers the reagents to the process tube. Mixing is performed in the process tube by 5 suck and dispense operations.
3. The robot places pipette tip #1 at its designated location in the reagent holder.
4. Heat the process tube to 60° C. and maintain it for 10 minutes.
5. After 5 minute of lysis, the robot picks up pipette tip #1 and mixes the contents by 3 suck and dispense operations.
6. The robot places pipette tip #1 at its designated location in the reagent holder.
7. After 10 minutes of lysis, a magnet is moved up the side of the process tube to a middle height of the sample and held at that position for a minute to capture all the magnetic beads against the wall the tube.

8. The magnet is brought down slowly to slide the captured beads close to the bottom (but not the bottom) of the tube.
9. Using pipette tip #2, aspirate all the liquid and dump it into the waste tube.
10. Aspirate a second time to remove as much liquid as possible from the process tube.
11. Using the same pipette tip #2, withdraw 100 µl of wash buffer and dispense it in the process tube. During this dispense, the magnet is moved downwards, away from the process tube.
12. Perform 15 mix steps to thoroughly mix the magnetic beads with the wash buffer.
13. Wait for 30 seconds.
14. Move magnet up to capture the beads to the side and hold for 15 seconds.
15. Using pipette tip #2, aspirate wash buffer twice to remove as much liquid as possible and dump it back in the wash tube.
16. Move magnet down away from the process tube.
17. Place pipette tip #2 in its specified location of the reagent holder.
18. Pick up a new pipette tip (tip #3) and withdraw 8-10 µl of release buffer and dispense it over the beads in the process tube.
19. Wait for 1 minute and then perform 45 mixes.
20. Heat the release solution to 85° C. and maintain temperature for 5 minutes.
21. Place pipette tip #3 in its specified location of the reagent holder.
22. Bring magnet up the tube, capture all the beads against the tube wall and move it up and away from the bottom of the tube.
23. Pick up a new pipette tip (tip #4) and withdraw all the release buffer from the process tube and then withdraw 3-10 µl of neutralization buffer, mix it in the pipette tip and dispense it in the PCR tube. (In case of two analyte detections, dispense half of the neutralized DNA solution into first PCR tube and the rest of the solution in the second PCR tube.
24. Using pipette tip #4, mix the neutralized DNA with the lyophilized reagents by 4-5 suck and dispense operations and withdraw the entire solution in the pipette tip.
25. Using pipette tip #4, load 6 µl of the final PCR solution in a lane of the 12-up cartridge.

Real-Time PCR

After all the appropriate PCR lanes of the PCR cartridge are loaded with final PCR solution, the tray containing the cartridge moves it in the PCR Analyzer. The cartridge is pressed by an optical detection read-head against the PCR heater. Heaters activate valves to close either ends of the PCR reactor and real-time thermocycling process starts. After completing appropriate PCR cycles (~45 cycles), the analyzer decides whether the sample has the target DNA based on the output fluorescence data, and issues an indication of the same.

Example 3: Exemplary Heater/Separator

Heaters for each of 24 process tubes, such as for carrying out lysis, can be individually software controlled. The lysis ramp times (e.g., the time that it takes for the water in a lysis tube to rise from a temperature of approximately 2.5° C. to a given temperature) can be less than 120 seconds for a rise to 50° C. and less than 300 seconds for a rise to 75° C. The lysis temperature (e.g., as measured in the water contained in a lysis tube) can be maintained, by the heaters, to within ±3° C. of the desired temperature. The accessible lysis temperature range can be from about 40° C. to about 82° C. Each of the heaters may draw about 16 Watts or more of power when in operation. The lysis heater can be designed to maximize the thermal transfer to the process tube, and also accommodate the tolerances of the various parts. The heaters can permit the tubes to be in direct contact with the magnets (described in more detail herein). The heaters may be adjustable in the horizontal plane during assembly and typically do not interfere with the covers of the system when installed.

Magnets are also included in the system, and the heater and magnet related mechanisms fit beneath a rack that contains a number of reagent holders, and do not interfere with rack insertion or registration. The magnets may be high-flux magnets (e.g., have about a 1,000 gauss, or greater, flux as measured within a given process tube), and be able to move a distance sufficient to achieve magnetic bead separation in one or more of the lysis tubes filled to a volume of 900 µL. The magnets can be software-controllable at movement rates from about 1 mm/sec to about 25 mm/sec. The wiring, included as part of the heater and controller assemblies, can be contained and protected from potential spills (e.g., spills of the process tubes). The magnets can be located about 1.25 inches or greater from the bottom of the lysis tube when not in use and can be retained in such a manner as to maximize contact with the lysis tube while also preventing jamming.

The foregoing description is intended to illustrate various aspects of the technology. It is not intended that the examples presented herein limit the scope of the technology. The technology now being fully described, it will be apparent to one of ordinary skill in the art that many changes and modifications can be made thereto without departing from the spirit or scope of the appended claims.

What is claimed is:
1. A method of extracting nucleic acids using a rack and an integrated separator and heater, the integrated separator and heater comprising a plurality of heater units aligned collinearly along a horizontal first axis, the integrated separator and heater further comprising one or more magnets disposed on a first side of the plurality of heater units and aligned along a second axis parallel to the first axis, the method comprising:
inserting a plurality of holders in the rack, each holder comprising a single process tube of a plurality of process tubes;
inserting the rack into the integrated separator and heater such that at least a portion of rack is removably received on a second side of the plurality of heater units opposite the one or more magnets on the first side, wherein a portion of each process tube of the plurality of process tubes is received in a single heater unit of the plurality of heater units when the rack is inserted into the integrated separator and heater;
moving all of the one or more magnets backwards and forwards together in a vertical direction perpendicular to the second axis while maintaining proximity to an exterior side of each of the process tubes received in the integrated separator and heater;
during at least a portion of the motion, moving magnetic particles contained in the process tubes; and
independently controlling each heater unit of the plurality of heater units to apply heat to the plurality of process tubes received in the integrated separator and heater.

2. The method of claim 1, wherein all of the one or more magnets are moved and the plurality of process tubes are heated at the same time.

3. The method of claim 1, wherein each heater unit comprises a cavity configured to partially surround a portion of the process tube received in the cavity.

4. The method of claim 3, wherein the cavity surrounds a lower portion of the process tube on two sides when the rack is inserted into the integrated separator and heater.

5. The method of claim 3, wherein the cavity surrounds a lower portion of the process tube on three sides when the rack is inserted into the integrated separator and heater.

6. The method of claim 3, further comprising sensing a temperature of each cavity.

7. The method of claim 1, wherein the one or more magnets are affixed to a supporting member, and wherein moving all of the one or more magnets comprising moving the supporting member.

8. The method of claim 7, wherein the supporting member is affixed to a shaft, and wherein moving all of the one or more magnets comprises moving the supporting member along the shaft.

9. The method of claim 8, further comprising moving the supporting member between a first position situated away from the plurality of process tubes, and a second position situated in close proximity to the plurality of process tubes.

10. The method of claim 9, further comprising moving the supporting member at an amplitude about the second position where the amplitude is smaller than a distance between the first position and the second position as measured along the shaft.

11. The method of claim 1, wherein the integrated separator and heater comprises 12 heater units.

12. The method of claim 1, wherein 12 holders are inserted in the rack.

13. The method of claim 1, wherein applying heat to the plurality of process tubes received in the integrated separator and heater comprises raising the temperature of a 1 ml sample in one of the process tubes from room temperature to about 65° C. in less than 3 minutes.

14. The method of claim 1, wherein moving the magnetic particles comprising moving the magnetic particles against a wall of the process tubes.

15. The method of claim 1, wherein moving the magnetic particles comprising concentrating the magnetic particles in a portion of the process tubes.

16. The method of claim 1, wherein moving the magnetic particles comprises sliding the magnetic particles toward the bottom of the process tubes.

17. The method of claim 1, wherein the magnetic particles are in suspension in solution in the process tubes, and wherein moving the magnetic particles comprises collecting the suspended magnetic particles into one location inside the process tubes.

18. The method of claim 17, further comprising aspirating the solution from the process tubes after collecting the suspended magnetic particles.

* * * * *